(12) United States Patent
Tavares et al.

(10) Patent No.: US 9,259,397 B2
(45) Date of Patent: Feb. 16, 2016

(54) LORATADINE TRANSDERMAL DEVICE AND METHODS

(75) Inventors: Lino Tavares, Kinnelon, NJ (US); Ihor Shevchuk, Yonkers, NY (US); Mark Alfonso, Easton, CT (US); Geraldine Marcenyac, Norwalk, CT (US); Kirti Valia, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 681 days.

(21) Appl. No.: 10/045,607

(22) Filed: Oct. 23, 2001

(65) Prior Publication Data

US 2003/0035828 A1 Feb. 20, 2003

Related U.S. Application Data

(60) Provisional application No. 60/242,515, filed on Oct. 23, 2000.

(51) Int. Cl.
| | |
|---|---|
| *A61K 9/70* | (2006.01) |
| *A61K 9/00* | (2006.01) |
| *A61K 47/38* | (2006.01) |
| *A61K 47/10* | (2006.01) |
| *A61K 31/55* | (2006.01) |
| *A61K 31/445* | (2006.01) |

(52) U.S. Cl.
CPC ............. *A61K 9/7053* (2013.01); *A61K 9/0014* (2013.01); *A61K 9/7061* (2013.01); *A61K 9/7069* (2013.01); *A61K 31/445* (2013.01); *A61K 31/55* (2013.01); *A61K 47/10* (2013.01); *A61K 47/38* (2013.01)

(58) Field of Classification Search
CPC . A61K 9/0095; A61K 31/445; A61K 9/7069; A61K 31/55; A61K 47/481; A61K 47/10; A61K 9/0014; A61K 9/7053; A61K 9/7061
USPC ......................................... 424/449, 443, 448
See application file for complete search history.

(56) References Cited

U.S. PATENT DOCUMENTS

| | | | |
|---|---|---|---|
| 4,659,716 A | 4/1987 | Villani et al. | |
| 4,910,205 A | 3/1990 | Kogan et al. | |
| 5,045,319 A * | 9/1991 | Chien et al. ................... | 424/448 |
| 5,091,186 A * | 2/1992 | Miranda et al. ................ | 424/448 |
| 5,225,199 A | 7/1993 | Hidaka et al. .................. | 424/443 |
| 5,240,711 A | 8/1993 | Hille et al. ..................... | 424/448 |

(Continued)

FOREIGN PATENT DOCUMENTS

| | | | | |
|---|---|---|---|---|
| WO | 9619975 | 12/1995 | ............... | A61K 9/70 |
| WO | WO 96/16641 | 6/1996 | | |
| WO | 9836728 | 8/1998 | ............. | A61K 13/00 |

OTHER PUBLICATIONS

Yie W. Chien and Kirti H. Valia; *Development of a Dynamic Skin Permeation System for Long-Term Permeation Studies*, Drug development and Industrial Pharmacy, 10(4), p. 575-599 (1984).

(Continued)

*Primary Examiner* — Isis Ghali
(74) *Attorney, Agent, or Firm* — Davidson, Davidson & Kappel, LLC

(57) ABSTRACT

A tansdermal delivery device for effectively treating seasonal allergic rhinitis and chronic idiopathic urticariain in humans is disclosed and methods thereof.

39 Claims, 14 Drawing Sheets

(56) References Cited

U.S. PATENT DOCUMENTS

| | | | |
|---|---|---|---|
| 5,879,701 A | 3/1999 | Audett et al. | 424/448 |
| 5,912,009 A * | 6/1999 | Venkateshwaran et al. | 424/448 |
| 5,968,547 A | 10/1999 | Reder et al. | 424/449 |
| 6,103,735 A | 8/2000 | Aslanian et al. | 514/290 |
| 6,315,854 B1 * | 11/2001 | Anhauser et al. | 156/267 |

OTHER PUBLICATIONS

Minutes of Oral Proceedings issued in European Patent Application No. 01 997 122.5 on Sep. 30, 2009.

Skelly, Jerome P. et al., "FDA and AAPS Report of the Workshop on Principles and Practices if In Vitro Percutaneous Penetration Studies: Relevance to Bioavailability and Bioequivalence," *Pharmaceutical Research*, vol. 4, No. 3 (1987), pp. 265-267.

* cited by examiner

LORATADINE TRANSDERMAL DEVICE AND METHODS

This application claims the benefit of U.S. Provisional Application No. 60/242,514, filed Oct. 23, 2000, hereby incorporated by reference.

BACKGROUND OF THE INVENTION

It is the intent of all sustained-release pharmaceutical preparations to provide a longer period of pharmacologic effect after the administration of a drug than is ordinarily experienced after the administration of immediate release preparations of the same drug. Such longer periods of efficacy can provide many inherent therapeutic benefits that are not achieved with corresponding immediate release preparations. The benefits of prolonged treatment of the nasal and non-nasal symptoms of seasonal allergic rhinitis or chronic idiopathic urticaria afforded by sustained release oral preparations have become universally recognized and oral sustained-release preparations are commercially available.

Another approach to sustained delivery of a therapeutically active agent is transdermal delivery systems, such as transdermal patches. Generally, transdermal patches contain a therapeutically active agent, a reservoir or matrix containing the active ingredient(s) and an adhesive which allows the transdermal device to adhere to the skin, allowing for the passage of the active agent from the device through the skin of the patient. Once the active agent has penetrated the skin layer, the drug is absorbed into the blood stream where it can exert a desired pharmacotherapeutic effect.

In spite of the known art related to transdermal therapy, there exists a need for the transdermal delivery of a beneficial agent for the treatment of seasonal allergic rhinitis and chronic idiopathic urticaria.

Loratadine, commercially available as Claritin® in the U.S. from Schering Corporation (Kenilworth, N.J. 07033, U.S.A.), is a long-acting tricyclic antihistamine with selective peripheral histamine H1-receptor antagonistic activity, with the chemical name, ethyl 4-(8-chloro-5,6-dihydro-11H-benzo cyclohepta pyridin-11-ylidene)-1-piperidinecarboxylate, and it is used mainly for treating nasal and non-nasal symptoms of seasonal allergic rhinitis, but may also be used in the treatment of chronic idiopathic urticaria, a common skin disorder. It is in the form of a white to off white powder, not soluble in water, but very soluble in organic solvents. Loratadine inhibits the activity of the substance, histamine, thus reducing the allergic effects caused by this substance such as itching, sneezing, runny nose and watery eyes. Loratadine is preferable to other antihistamines because it is nonsedating and does not cause cardiac arrhythmias brought on by use of some other antihistamines. The recommended oral dosage of loratadine for adults and children 12 years old or older is 10 mg once daily. In patients with liver or renal problems, the initial oral dosage of loratadine should be 10 mg every other day.

Seasonal allergic rhinitis (hay fever) is a term used to describe the symptoms caused seasonally by an allergic reaction that occurs in the eyes, nose, and throat in response to airborne allergens such as pollen from trees, grasses, and weeds. Other possible allergens include dust mites, molds, and animal dander. The allergens produce an allergic response by misleading the immune into thinking that the allergen is a harmful substance, thereby causing the immune system to produce antibodies to this specific allergen. When that allergen enters the immune system again, a reaction occurs between the allergen and IgE antibodies triggering the release of substances such as histamine from mast cells and other cells, producing symptoms such as runny nose, watery eyes, sneezing, and itching.

Chronic urticaria is an allergic skin disorder characterized by hives, e.g. red welts or small bumps, on the skin which are very itchy. Patients with chronic urticaria have hives that last longer than six months. This skin disorder is caused by an antigen-antibody reaction in which histamine and other substances such as acetyl choline are released from mast cells and other cells causing symptoms such as swelling, itching, pain, and rash. There are also cases in which there are no known causes for the hives (chronic idiopathic urticaria). As with chronic urticaria, antihistamines are used for treating chronic idiopathic urticaria.

Symptoms of seasonal allergic rhinitis and chronic idiopathic urticaria are improved by treatment with nonsedating antihistamines. Nonsedating antihistamines such as loratadine (The Merck Index, $11^{th}$ Edition, Merck & Co., Inc., Rahway, N.J. U.S.A. 1989, hereby incorporated by reference) act as an antagonist to the peripheral histamine $H_1$ receptor by selectively binding to this receptor, thereby blocking histamine from being released from the immune system and thus preventing histamines unwanted effects. (Goodman and Gillmans, The Pharmacological Basis of Therapeutics, $9^{th}$ Edition, hereby incorporated by reference).

Following oral administration, loratadine is rapidly absorbed, fast acting, and undergoes extensive first pass metabolism to the active metabolite descarboethoxyloratadine. Food delays absorption, so loratadine should be taken on an empty stomach. Pharmacokinetic studies have revealed that the onset of antihistamine activity occurs within 1-3 hours following administration of loratadine, reaching a maximum at 8-12 hours and lasting in excess of 24 hours. There was no evidence of tolerance to this effect after 28 days of dosing with loratadine. After 10 days of dosing, a mean peak plasma concentration of 1.3 hours and 2.3 hours ($T_{max}$) was observed in loratadine and the active metabolite, respectively. The mean elimination half-life observed in normal adults was 8.4 hours for loratadine and 28 hours for active metabolite. In patients with chronic liver disease, a mean half-life for loratadine and descarboethoxyloratadine of 24 hours and 37 hours were observed, respectively. Within 10 days of dosing, approximately 80% of the total loratadine administered were found in equal proportions between the urine and feces in the form of metabolic products. Finally, loratadine is 97% plasma-protein bound.

The most common adverse side effects of loratadine therapy include headache, somnolence, fatigue, and dry mouth. Less common or rare side effects may include altered lacrimination, altered salivation, flushing, hypoesthesia, impotence, increased sweating, thirst, angioneurotic edema, asthenia, back pain, blurred vision, chest pain, earache, eye pain, fever, leg cramps, malaise, rigors, tinnitus, viral infection, weight gain, hypertension, hypotension, palpitations, superventricular tachyarrhythmias, syncope, tachycardia, blepharospasm, dizziness, dysphonia, hypertonia, migraine, paresthesia, tremor, vertigo, altered taste, anorexia, constipation, diarrhea, dyspepsia, flatulence, gastritis, hiccup, increased appetite, nausea, stomatitis, toothache, vomiting, arthraglia, myalgia, agitation, amnesia, anxiety, confusion, decreased libido, depression, impaired concentration, insomnia, irritability, paroniria, breast pain, dysmenorrhea, menorrhagia, vaginitis, bronchitis, bronchospasm, coughing, dyspnea, epistaxis, hemoptysis, laryngitis, nasal dryness, pharyngitis, sinusitis, sneezing, dermatitis, dry hair, dry skin, photosensitivity reaction, pruritis, purpura, rash, urticaria, altered micturition, urinary discoloration, urinary incontinence, urinary retention. Further, the following spontaneous adverse effects were rarely reported for loratadine: abnormal hepatic function, including jaundice, hepatitis, and hepatic necrosis, alopecia, anaphylaxis, breast enlargement, erythema multiforme, peripheral edema, and seizures. (Physicians' Desk Reference, 53rd Edition, 1999, hereby incorporated by reference).

Despite advances in the art, there remains a need for methods of treating patients with seasonal allergic rhinitis and chronic idiopathic urticaria with an agent that provides effective levels of loratadine for prolonged periods of time, preferably while eliminating or minimizing the symptoms of seasonal allergic rhinitis or chronic idiopathic urticaria, and/or any of the other above mentioned side effects, thus providing a safe and effective method of management of such allergic reactions and skin disorders.

OBJECTS AND SUMMARY OF THE INVENTION

It is an object of the present invention to provide a continuous plasma loratadine concentration in mammals, preferably humans patients suffering from seasonal allergic rhinitis and/or chronic idiopathic urticaria.

It is an object of certain embodiments of the present invention to provide a method for treating patients suffering from seasonal allergic rhinitis and chronic idiopathic urticaria which achieves prolonged and effective management of these conditions, while at the same time provides the opportunity to reduce possible side effects, e.g., which patients may experience when subjected to prolonged oral therapy.

It is an object of certain embodiments of the present invention to provide a method for the treatment of seasonal allergic rhinitis and chronic idiopathic urticaria disorders in patients by utilizing a transdermal delivery system which contains loratadine.

It is an object of certain embodiments of the present invention to provide a method for the treatment of seasonal allergic rhinitis and chronic idiopathic urticaria disorders in patients which maximizes the dosage interval, i.e., the interval during which the transdermal delivery system is maintained in contact with the skin, and minimizes the plasma concentrations and or fluctuations in plasma concentrations in the patients during the dosage interval, while surprisingly maintaining effective management of seasonal allergic rhinitis and chronic idiopathic urticaria.

It is an object of certain embodiments of the present invention to provide a method for lessening the dry mouth associated with the oral administration of loratadine.

In certain embodiments, the present invention is directed to a method of effectively treating seasonal allergic rhinitus, chronic idiopathic urticaria, or both conditions in a human patient, comprising
administering loratadine transdermally to the human patient by applying a transdermal delivery system containing loratadine to the skin of a patient, and maintaining the transdermal delivery system in contact with the skin of the patient for at least 3 days, the transdermal delivery system maintaining an effective mean relative release rate to provide a therapeutic blood level of the loratadine within 36 hours from the initiation of the dosing interval, and thereafter maintaining a therapeutic blood level until the end of at least the three-day dosing interval.

In certain embodiments, the present invention is directed to a method of effectively treating seasonal allergic rhinitus, chronic idiopathic urticaria, or both conditions in a human patient, comprising
administering loratadine transdermally to the human patient by applying a transdermal delivery system containing loratadine to the skin of a patient, and maintaining the transdermal delivery system in contact with the skin of the patient for at least 5 days, the transdermal delivery system maintaining an effective mean relative release rate to provide a therapeutic blood level of the loratadine within three days from the initiation of the dosing interval, and thereafter maintaining a therapeutic blood level until the end of at least the five-day dosing interval.

In certain embodiments, the present invention is directed to a method for lessening the incidence of side-effects in a patient associated with the oral administration of loratadine, wherein the method comprises administering the loratadine in a transdermal delivery system over at least twenty-four hours and thereby lessening the incidence of side effects.

In certain embodiments, the above methods can further comprise providing a mean relative release rate of loratadine from a transdermal delivery system to provide a plasma level of loratadine of at least about 0.1 ng/ml within about 6 hours, 3 hours, 2 hours, 1 hour or 0.5 hours after after application of the transdermal delivery system onto the skin of the patient.

In certain embodiments, the above methods can further comprise providing a loratadine transdermal delivery system which maintains a plasma level of loratadine at steady-state from about 1 to about 3 ng/ml.

In certain embodiments, the above methods can further comprise maintaining a therapeutic plasma level from about 0.1 ng/ml to about 3.3 ng/ml during the dosing interval for the transdermal delivery system.

In certain embodiments, the above methods can further comprise having the transdermal delivery system having a mean relative release rate from 1.0 μm/hour/cm$^2$ to about 30.0 μm/hour/cm$^2$ or about 1.8 μm/hour/cm$^2$ to about 17 μm/hour/cm$^2$.

In certain other embodiments, the above methods can further comprise having the transdermal delivery system having a mean relative release rate from 2.0 μm/hour/cm$^2$ to about 10.0 μm/hour/cm$^2$.

In certain other embodiments, the above methods can further comprise having the transdermal delivery system having a mean relative release rate from 2.0 μm/hour/cm$^2$ to about 5.0 μm/hour/cm$^2$.

In certain embodiments, the above methods can further comprise having the transdermal delivery system having a mean relative release rate from about 2.8 μg/cm$^2$/hr to about 16.2 μg/cm$^2$/hr at 24 hours;
from about 2.3 μg/cm$^2$/hr to about 13.7 μg/cm$^2$/hr at 48 hours; and
from about 2.0 μg/cm$^2$/hr to about 11.9 μg/cm$^2$/hr at 72 hours; as determined via an in-vitro permeation test utilizing a Valia-Chien cell where the membrane is a human cadaver skin and the cell has a receptor chamber containing a 40:60 mixture of ethanol:water.

In certain embodiments, the above methods can further comprise having the transdermal delivery system to provide an in-vitro cumulative amount of permeation of from about 63 μg/cm$^2$ to about 388 μg/cm$^2$ at 24 hours; from about 105 μg/cm$^2$ to about 660 μg/cm$^2$ at 48 hours; and from about 139 μg/cm$^2$ to about 854 μg/cm$^2$ at 72 hours, as determined via an in-vitro permeation test utilizing a Valia-Chien cell where the membrane is a human cadaver skin and the cell has a receptor chamber containing a 40:60 mixture of ethanol:water.

In certain embodiments, the above methods can further comprise having the plasma level of loratadine at 48 hours not decrease by more than 30% over the next 72 hours.

In certain embodiments, the above methods can further comprise maintaining an effective mean relative release rate of the transdermal delivery system to provide a substantially first order plasma level increase of loratadine from the initiation of the dosing interval until about 48 to about 72 hours after the initiation of the dosing interval; and thereafter providing an effective mean relative release rate to provide a substantially zero order plasma level fluctuation of loratadine until the end of at least the five-day dosing interval.

In certain embodiments, the above methods can further comprise administering the loratadine in a transdermal delivery system applied to the skin of a human patient for about 3 to about 5 days.

In certain embodiments, the invention is directed to a transdermal device containing loratadine which provides effective blood plasma levels of loratadine when the device is applied to the skin of a mammal, preferably a human.

In certain embodiments, the invention is directed to a transdermal device containing loratadine which provides effective treatment of seasonal allergic rhinitis and chronic idiopathic urticaria disorders in patients.

In certain embodiments, the invention is directed to a transdermal delivery device comprising loratadine or a pharmaceutically acceptable salt thereof which maintains an effective mean relative release rate to provide a therapeutic blood level of the loratadine within three days from the initiation of the dosing interval, and thereafter maintaining a therapeutic blood level until the end of at least the five-day dosing interval.

In certain embodiments, the invention is directed to a transdermal device containing loratadine for the treatment of seasonal allergic rhinitis and chronic idiopathic urticaria disorders in patients which maximizes the dosage interval, i.e., the interval during which the transdermal delivery system is maintained in contact with the skin, and minimizes the plasma concentrations and or fluctuations in plasma concentrations in the patients during the dosage interval, while surprisingly maintaining effective management of seasonal allergic rhinitis and chronic idiopathic urticaria.

In certain embodiments, the invention is directed to a transdermal delivery system containing loratadine or a pharmaceutically acceptable salt thereof which provides a mean relative release rate from about 1.0 μm/hour/cm$^2$ to about 30.0 μm/hour/cm$^2$ or about 1.8 μm/hour/cm$^2$ to about 17 μm/hour/cm$^2$ of the transdermal delivery system; a plasma level of loratadine of at least about 0.1 ng/ml within about 6 hours, 3 hours, 2 hours, 1 hour or 0.5 hours after application of the transdermal delivery system onto the skin of the patient; and a plasma level of loratadine at steady-state from about 0.1 to about 3.3 ng/ml.

In certain embodiments, the transdermal delivery system provides a mean relative release rate from about 2.8 μg/cm$^2$/hr to about 16.2 μg/cm$^2$/hr at 24 hours; from about 2.3 μg/cm$^2$/hr to about 13.7 μg/cm$^2$/hr at 48 hours; and from about 2.0 μg/cm$^2$/hr to about 11.9 μg/cm$^2$/hr at 72 hours; as determined via an in-vitro permeation test utilizing a Valia-Chien cell where the membrane is a human cadaver skin and the cell has a receptor chamber containing a 40:60 mixture of ethanol:water.

In certain embodiments, the transdermal delivery system provides an in-vitro cumulative amount of permeation of from about 63 μg/cm$^2$ to about 388 μg/cm$^2$ at 24 hours; from about 105 μg/cm$^2$ to about 660 μg/cm at 48 hours; and from about 139 μg/cm$^2$ to about 854 μg/cm at 72 hours, as determined via an in-vitro permeation test utilizing a Valia-Chien cell where the membrane is a human cadaver skin and the cell has a receptor chamber containing a 40:60 mixture of ethanol:water.

In certain embodiments, the transdermal delivery system maintains a plasma level of loratadine at steady-state from about 1 to about 3 ng/ml.

In certain embodiments, the transdermal delivery system maintains an effective mean relative release rate to provide a therapeutic blood level of the loratadine within three days from the initiation of the dosing interval, and thereafter maintaining a therapeutic blood level until the end of at least the five-day dosing interval.

In certain embodiments, the transdermal delivery system provides a mean relative release rate of loratadine effective to provide a plasma level of loratadine of at least about 0.1 ng/ml within about 6 hours, 3 hours, 2 hours, 1 hour or 0.5 hours after application of the transdermal delivery system onto the skin of the patient.

In certain embodiments, the transdermal delivery system maintains a plasma level of loratadine at steady-state from about 1 to about 3 ng/ml.

In certain embodiments, the transdermal delivery system maintains a therapeutic plasma level from about 0.1 ng/ml to about 3.3 ng/ml during the dosing interval for the transdermal delivery system.

In certain embodiments, the transdermal delivery system provides a mean relative release rate from about 1.0 μm/hour/cm$^2$ to about 30.0 μm/hour/cm$^2$ or about 1.8 μg/hour/cm$^2$ to about 17 μg/hour/cm$^2$ of the transdermal delivery system.

In certain embodiments, the transdermal delivery system provides a mean relative release rate from about 2.8 μg/cm$^2$/hr to about 16.2 μg/cm$^2$/hr at 24 hours; from about 2.3 μg/cm$^2$/hr to about 13.7 μg/cm$^2$/hr at 48 hours; and from about 2.0 μg/cm$^2$/hr to about 11.9 μg/cm$^2$/hr at 72 hours; and from about 1.8 μg/cm$^2$/hr to about 9.9 μg/cm$^2$/hr at 96 hours; as determined via an in-vitro permeation test utilizing a Valia-Chien cell where the membrane is a human cadaver skin and the cell has a receptor chamber containing a 40:60 mixture of ethanol:water.

In certain embodiments, the transdermal delivery system provides an in-vitro cumulative amount of permeation of from about 63 μg/cm to about 388 μg/cm$^2$ at 24 hours; from about 105 μg/cm$^2$ to about 660 μg/cm$^2$ at 48 hours; and from about 139 μg/cm$^2$ to about 854 μg/cm$^2$ a 72 hours; and from about 162 μg/cm$^2$ to about 955 μg/cm$^2$ at 96 hours; as determined via an in-vitro permeation test utilizing a Valia-Chien cell where the membrane is a human cadaver skin and the cell has a receptor chamber containing a 40:60 mixture of ethanol:water.

In further embodiments, the invention is directed to a transdermal device and method which, when applied to the skin of a mammal such as a human patient, provides therapeutically effective blood plasma levels of loratadine to effectively treat seasonal allergic rhinitis, chronic idiopathic urticaria, or both conditions in a human patient, wherein the transdermal device is maintained in contact with the patient's skin for at least 5 days, the transdermal delivery system maintaining an effective mean relative release rate to provide a therapeutic blood level of the loratadine within three days from the initiation of the dosing interval, and thereafter maintaining a therapeutic blood level until the end of at least the five-day dosing interval.

The invention is further directed to a transdermal loratadine device for the effective treatment of seasonal allergic rhinitis, chronic idiopathic urticaria, or both conditions in a human patient, which device, when applied to the skin of a patient maintained in contact with the patient's skin for at least 3 days, has an effective mean relative release rate to provide a therapeutic blood level of the loratadine within 36 hours from the initiation of the dosing interval, and thereafter maintains a therapeutic blood level until the end of at least the three-day dosing interval.

The invention is further directed in part to a transdermal loratadine device for the treatment of chronic allergic rhinitis and chronic idiopathic urticaria which provides substantially zero order pharmacokinetics over a significant portion of the dosage interval.

The invention is further directed to a transdermal device and a method of effectively treating seasonal allergic rhinitis, chronic idiopathic urticaria, or both conditions in a human patient, comprising applying the transdermal loratadine device to the skin of the patient and maintaining the transdermal delivery system in contact with the skin of a patient for at least 5 days, the transdermal delivery system maintaining an effective mean relative release rate to provide a substantially first order plasma level increase of loratadine from the initiation of the dosing interval until about 48 to about 72 hours after the initiation of the dosing interval; and thereafter providing an effective mean relative release rate to provide a substantially zero order plasma level fluctuation of loratadine until the end of at least the five-day dosing interval.

The invention is further directed to a transdermal loratadine device which when applied to the skin of a patient and maintained in contact with the patient's skin for at least 3 days, has an effective mean relative release rate to provide a substantially first order plasma level increase of loratadine from the initiation of the dosing interval until about 24 hours after the initiation of the dosing interval; and thereafter provides an effective mean relative release rate to provide a substantially zero order plasma level fluctuation of loratadine until the end of at least the three-day dosing interval.

The invention is further directed to a transdermal loratadine device and a method for lessening the incidence of side-effects in a patient associated with the oral administration of loratadine, wherein the method comprises administering the loratadine in a transdermal dosage form over at least twenty-four hours and thereby lessening the incidence of side effects.

The invention is further directed to a transdermal loratadine device and method which provides for reduced side-effects and for avoids peak plasma concentrations of loratadine in a patient associated with the oral administration of loratadine (i.e., reduces the peak plasma level relative to immediate release orally delivered loratadine), via the administration of loratadine in a transdermal dosage form over at least twenty-four hours, thereby lessening the incidence of side effects and avoiding the peak plasma concentrations of loratadine.

In certain embodiments, the invention is directed to transdermal delivery devices which are suitable for attaining any of the above methods.

For example, the above methods can be achieved utilizing a transdermal therapeutic system for the administration of loratadine to the skin comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of loratadine base or of a pharmaceutically acceptable salt thereof and 0.1 to 30% of a solvent for the loratadine or salt thereof.

Another alternative is to utilize a laminated composite for administering loratadine or a pharmaceutically acceptable salt thereof to an individual transdermally comprising (a) a polymer backing layer that is substantially impermeable to loratadine or the pharmaceutically acceptable salt thereof; and
(b) a reservoir layer comprising an acrylate or silicone pressure-sensitive adhesive, 0.1 to 20% of loratadine base or of a pharmaceutically acceptable salt thereof, 0.1 to 30% of an ester of a carboxylic acid acting as a softening agent and 0.1 to 30% of a solvent for loratadine having at least one acidic group.

The methods of the present invention are described in further detail in the following sections. Unless defined otherwise, all technical and scientific terms used herein have the same meaning as commonly understood by one of ordinary skill in the art to which this invention pertains. However, it should be understood that for purposes of the present invention, the following terms have the following meanings:

The term "effective treatment of seasonal allergic rhinitis or chronic idiopathic urticaria" is defined for purposes of the present invention as a satisfactory reduction in or elimination of the symptoms associated with seasonal allergic rhinitis and chronic idiopathic urticaria, along with the process of a tolerable level of side effects, as determined by the human patient.

Drug release from membrane-controlled systems may be defined as follows:

$$\text{Amount released per area unit } Q = \text{const (zero order kinetics)}$$

The term "mean relative release rate" is determined from the amount of drug released per unit time from the transdermal delivery system through the skin and into the bloodstream of a human patient. Mean relative release rate may be expressed, e.g., as $\mu g/cm^2/hr$. For example, a transdermal delivery system that releases 10 mg of loratadine over a time period of 24 hours is considered to have a relative release rate of 420 $\mu g/hr$. For purposes of the invention, it is understood that relative release rates may change between any particular time points within a particular dosing interval, and the term therefore only reflects the overall release rate during the particular dosing interval. For purposes of the present invention, relative release rate should be considered synonymous with the term "flux rate".

The term "sustained release" is defined for purposes of the present invention as the release of the drug (loratadine) from the transdermal formulation at such a rate that blood (e.g., plasma) concentrations (levels) are maintained within the therapeutic range (above the minimum effective concentration) but below the upper limit of the therapeutic window over a period of time of about 3 days or longer.

The term "steady state" means that the blood plasma concentration curve for a given drug has been substantially repeated from dose to dose.

The term "minimum effective concentration" is defined for purposes of this invention as the minimum effective therapeutic blood plasma level of the drug at which at least some therapeutic effect in treating seasonal allergic rhinitis or chronic idiopathic urticaria is achieved in a given patient.

The term "overage" means for the purposes of the present invention the amount of loratadine contained in a transdermal delivery system which is not delivered to the patient. The overage is necessary for creating a concentration gradient by means of which the active agent (e.g., loratadine) migrates through the layers of the transdermal dosage form to the desired site on a patient's skin.

The term "first order" pharmacokinetics is defined as plasma concentrations which increase over a specified time period.

The term "zero order" pharmacokinetics contemplates an amount of drug released from a loratadine formulation which substantially maintains plasma concentrations at a relatively constant level. For purposes of the present invention, a relatively constant plasma concentration is defined as a concentration which does not decrease more than about 30% over a 48 hour time period.

Drug release from membrane-controlled systems may be defined as follows:

Amount released per area unit $Q$=const (zero order kinetics)

The term "mean relative release rate" is determined from the amount of drug released per unit time from the transdermal delivery system through the skin and into the bloodstream of a human patient. Mean relative release rate may be expressed, e.g., as $\mu g/cm^2/hr$. For example, a transdermal delivery system that releases 10 mg of loratadine over a time period of 24 hours is considered to have a relative release rate of $4.1 \times 10^{-4}$ $\mu g/hr$. For purposes of the invention, it is understood that relative release rates may change between any particular time points within a particular dosing interval, and the term therefore only reflects the overall release rate during the particular dosing interval. For purposes of the present invention, relative release rate should be considered synonymous with the term "flux rate".

The term "sustained release" is defined for purposes of the present invention as the release of the drug from the transdermal formulation at such a rate that blood (e.g., plasma) concentrations (levels) are maintained within the therapeutic range (above the minimum effective drug concentration or "MEDC") but below toxic levels over a period of time of about 3 days or longer.

The term "steady state" means that the blood plasma concentration curve for a given drug has been substantially repeated from dose to dose.

The term "minimum effective concentration" is defined for purposes of this invention as the minimum effective therapeutic blood plasma level of the drug at which at least some relief of the seasonal allergic rhinitis or chronic idiopathic urticaria symptoms is achieved in a given patient.

For purposes of the present invention, the term "loratadine" shall include loratadine base, pharmaceutically acceptable salts thereof, stereoisomers thereof, enantiomers thereof, ethers thereof, and mixtures thereof.

For purposes of the present invention, the terms "transdermal delivery device" and "transdermal delivery system" are interchangeable.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
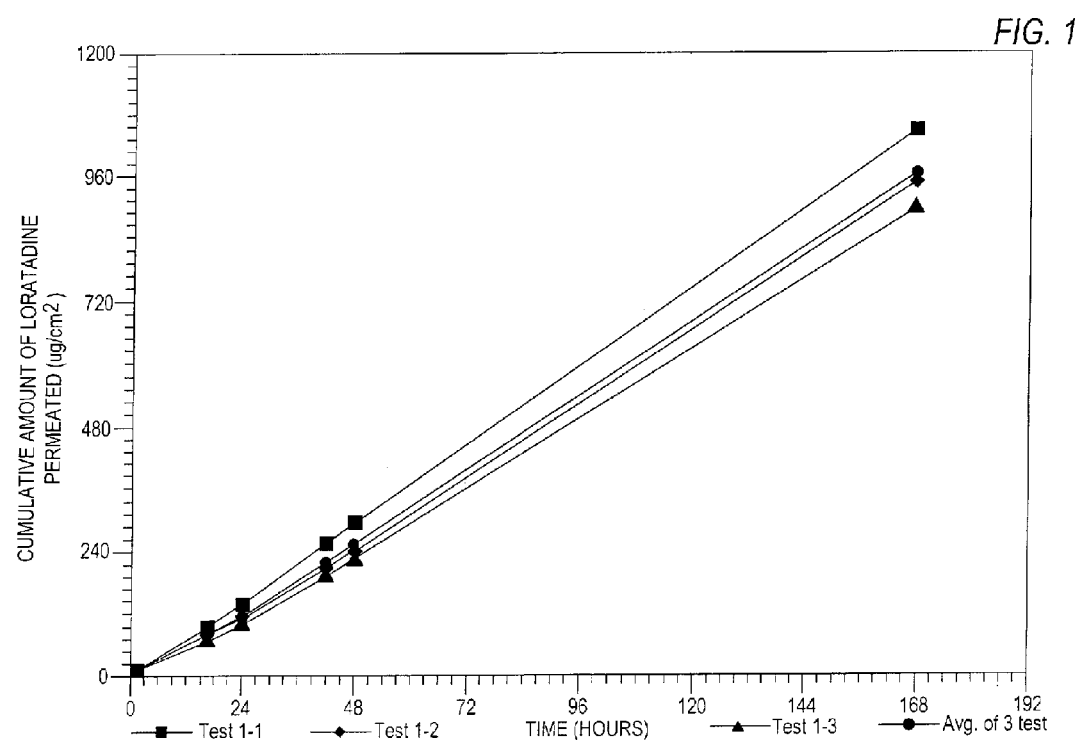
FIG. 1 is a graphical representation of the cumulative amounts of loratadine resulting from 3 permeation tests of Example 1 through human cadaver skin.
Figure 2:
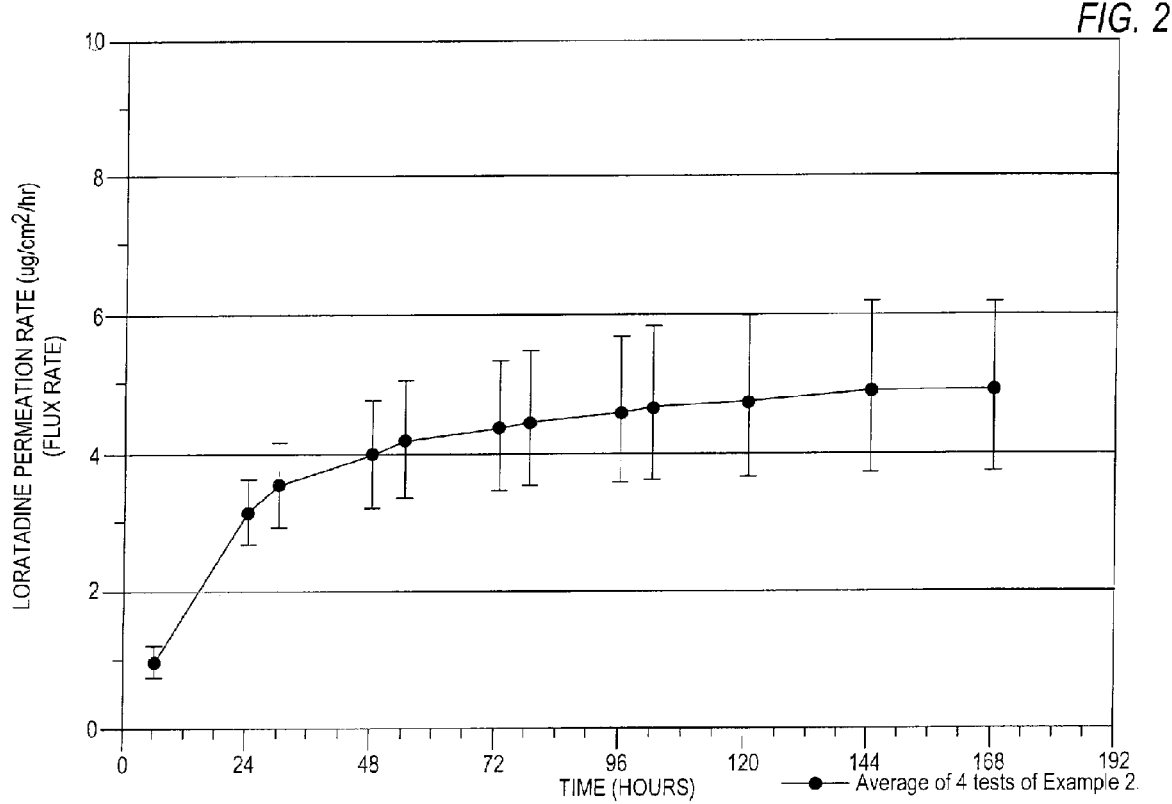
FIG. 2 is a graphical representation of the average loratadine permeation rate (flux rate) of Example 2 through human cadaver skin.
Figure 3:
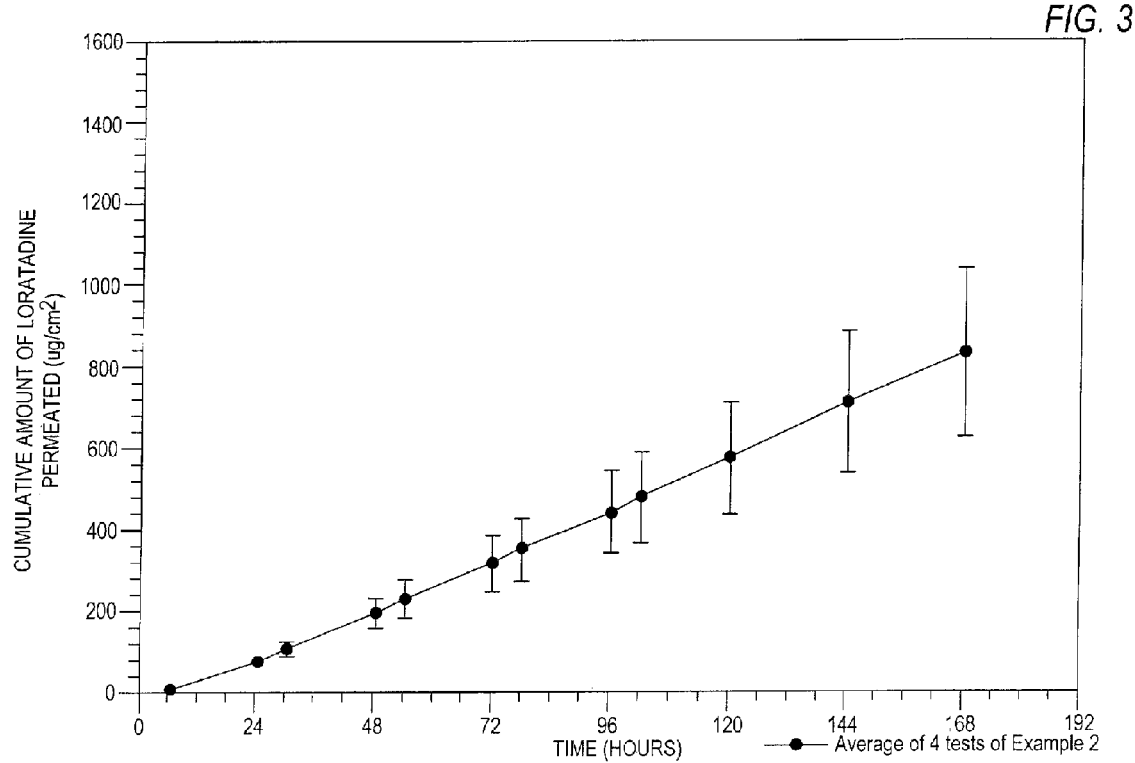
FIG. 3 is a graphical representation of the average cumulative amount of loratadine resulting from 4 permeation tests of Example 2 through human cadaver skin.
Figure 4:
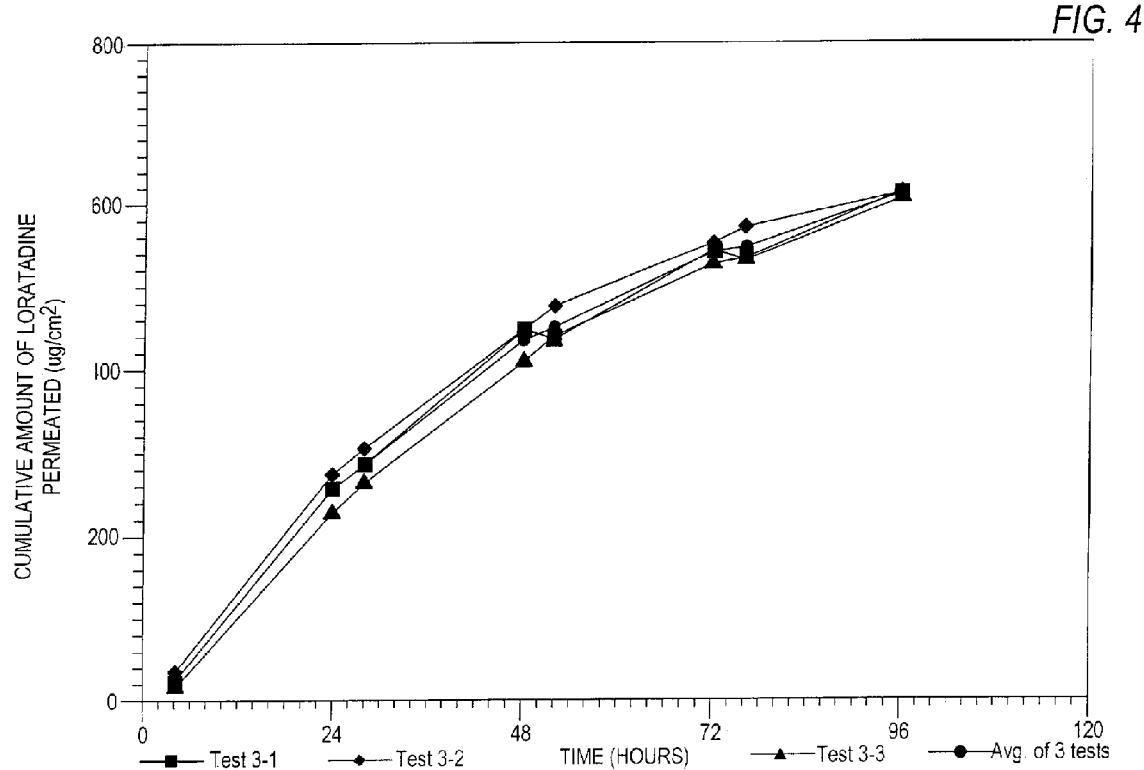
FIG. 4 is a graphical representation of the cumulative amounts of loratadine resulting from 3 permeation tests of Example 3 through human cadaver skin.
Figure 5:
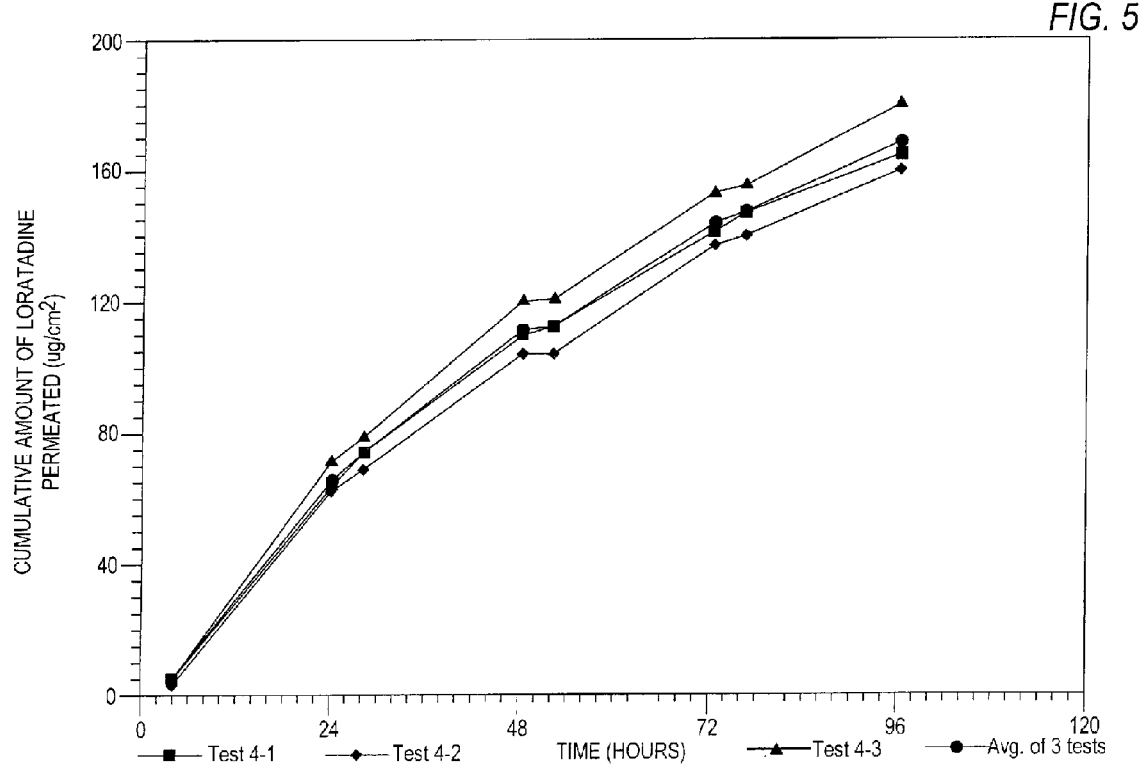
FIG. 5 is a graphical representation of the cumulative amounts of loratadine resulting from 3 permeation tests of Example 4 through human cadaver skin.
Figure 6:
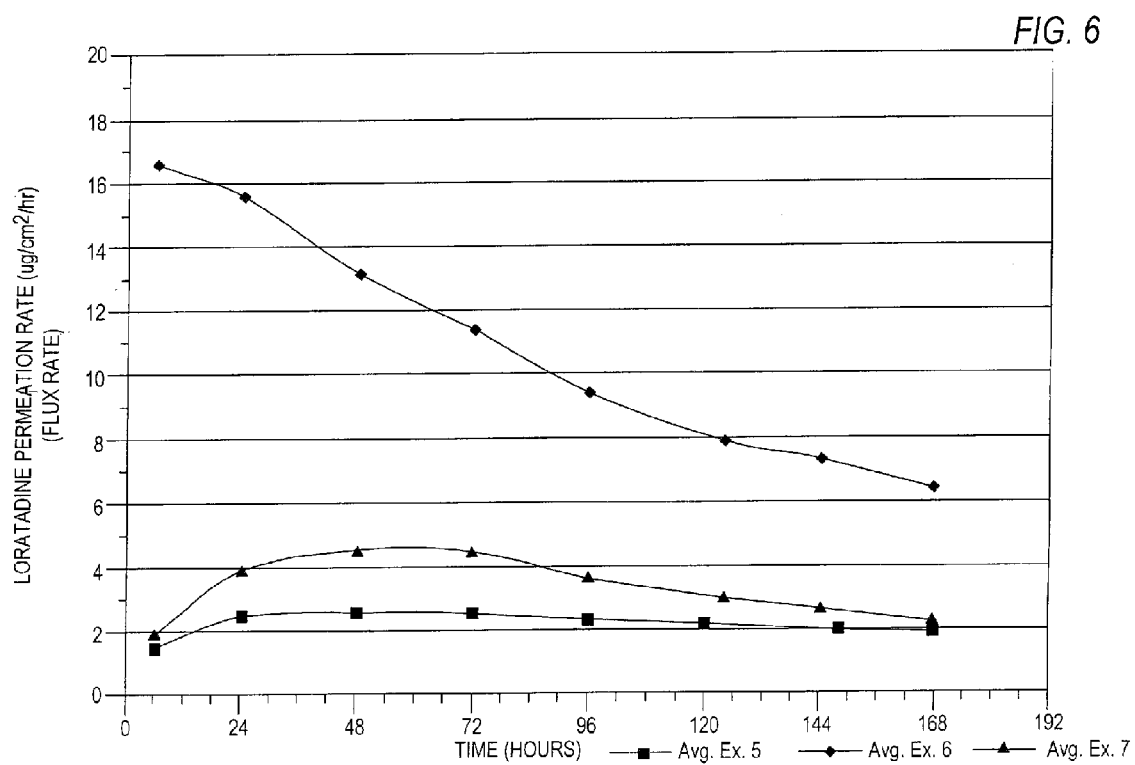
FIG. 6 is graphical representation of the average loratadine permeation rates (flux rates) of Examples 5, 6, and 7 through human cadaver skin.
Figure 7:
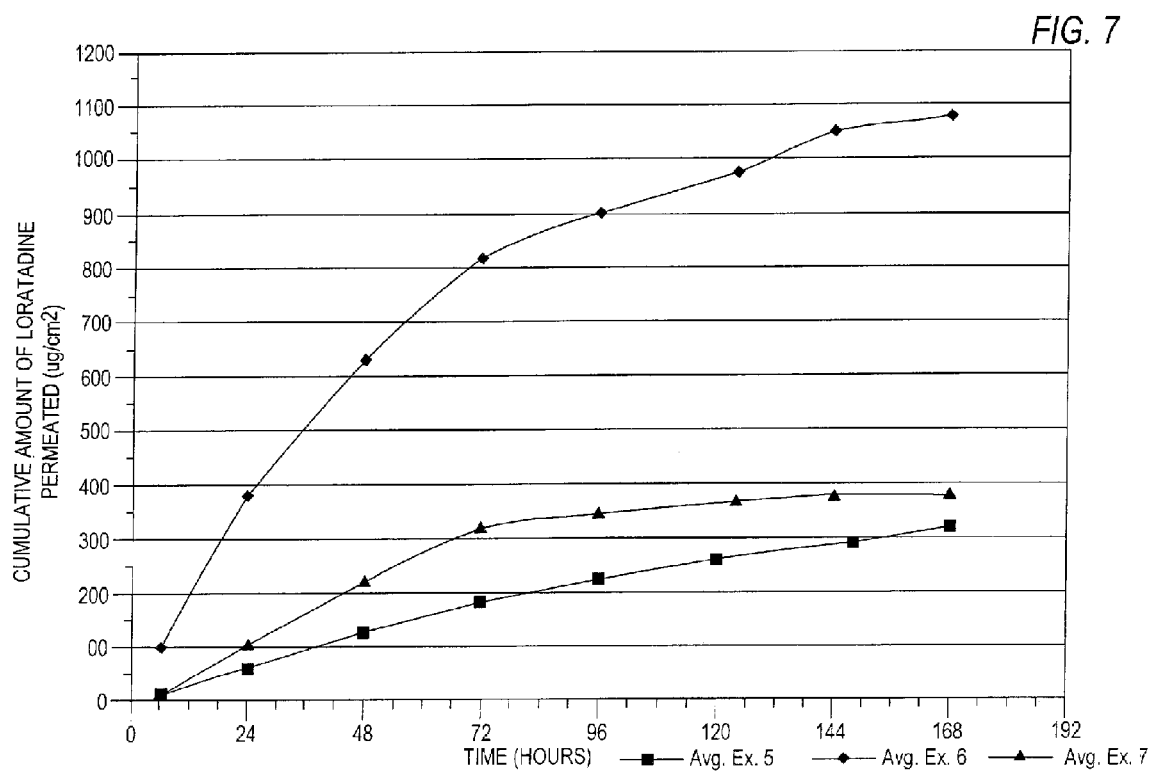
FIG. 7 is a graphical representation of the average cumulative amounts of loratadine resulting from permeation tests of Examples 5, 6, and 7 through human cadaver skin.
Figure 8:
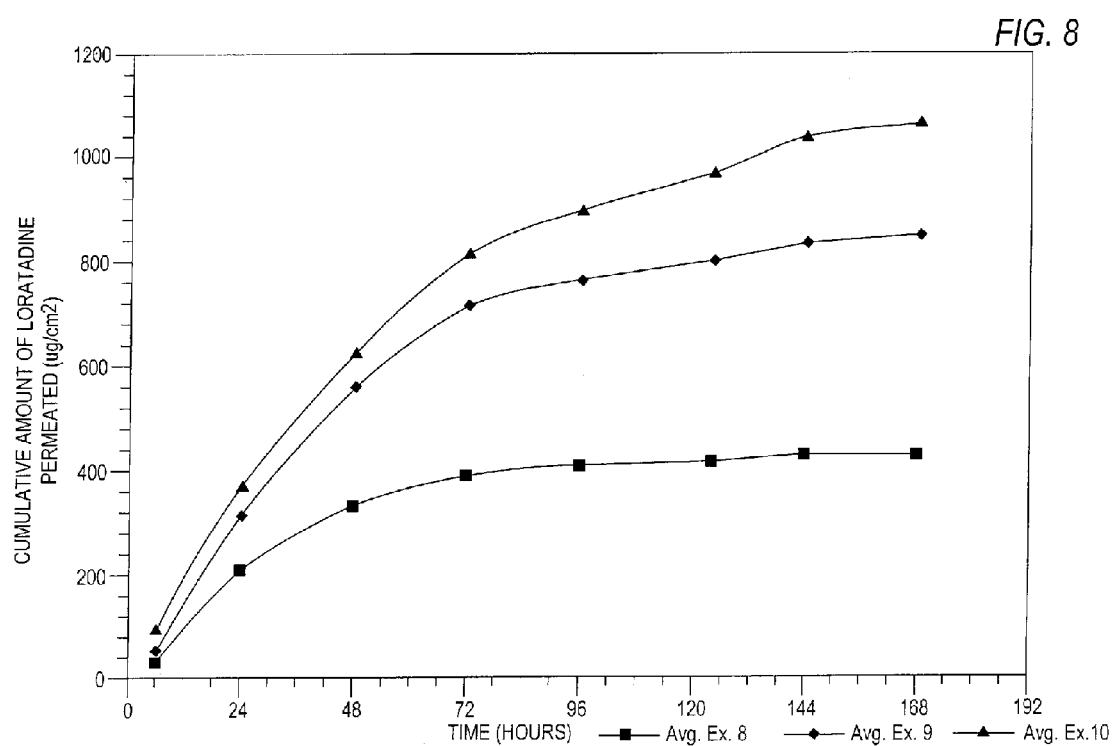
FIG. 8 is a graphical representation of the average cumulative amounts of loratadine resulting from permeation tests of Examples 8, 9, and 10 through human cadaver skin.
Figure 9:
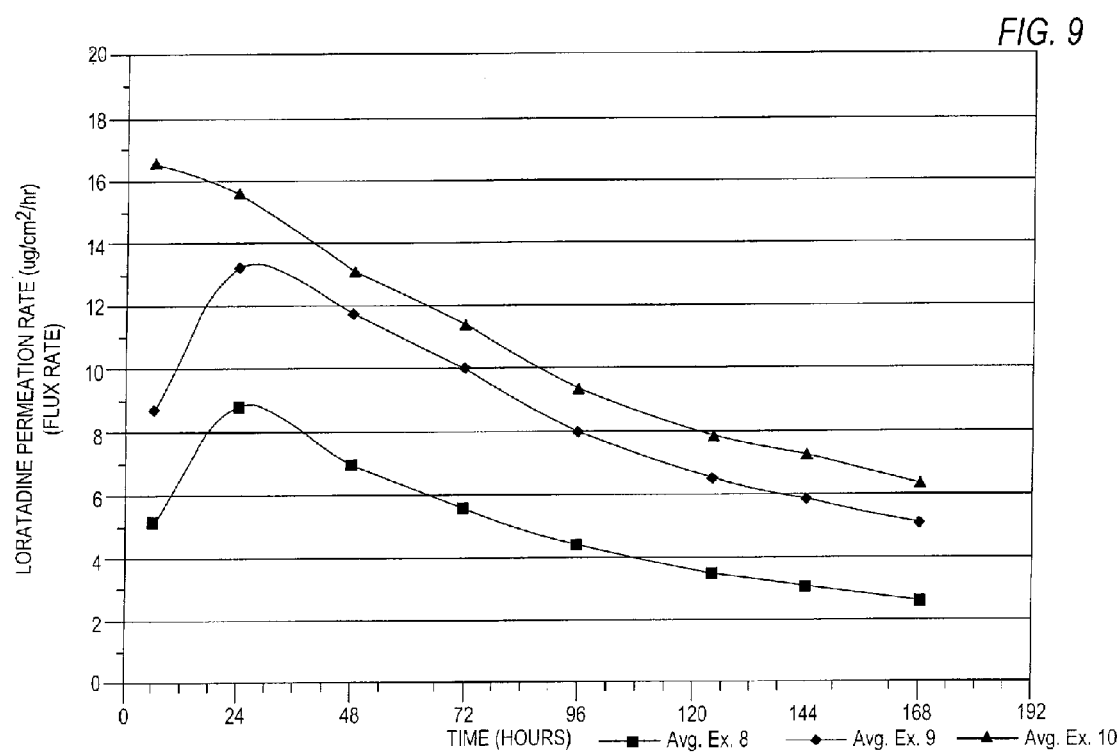
FIG. 9 is a graphical representation of the average loratadine permeation rates (flux rates) of Examples 8, 9, and 10 through human cadaver skin.
Figure 10:
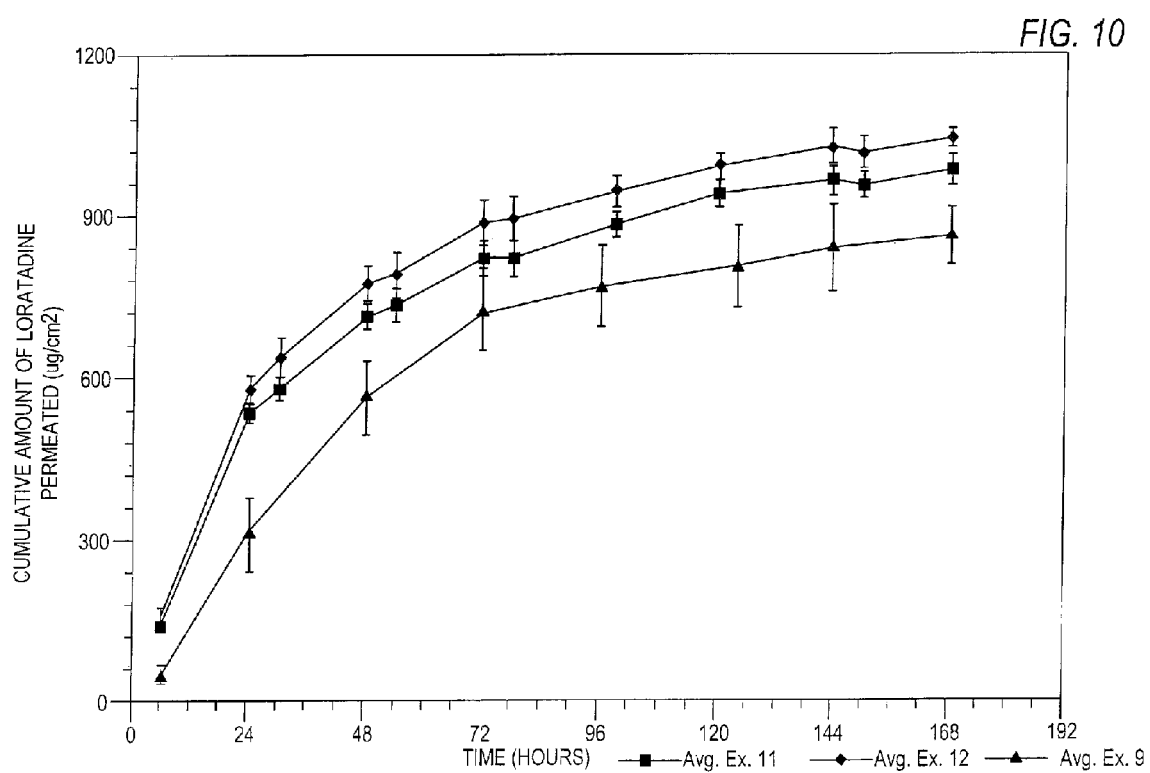
FIG. 10 is a graphical representation of the average cumulative amounts of loratadine resulting from permeation tests of Examples 11, 12, and 9 through human cadaver skin.
Figure 11:
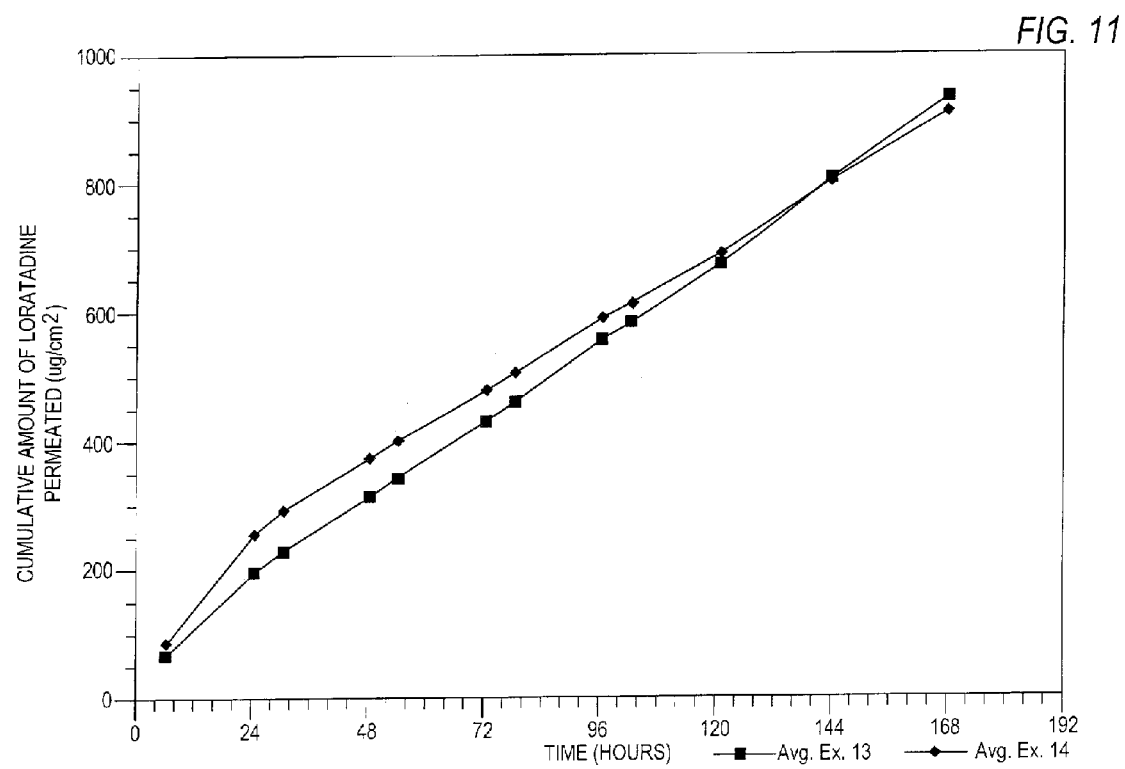
FIG. 11 is a graphical representation of the average cumulative amounts of loratadine resulting from permeation tests of Examples 13 and 14 through human cadaver skin.
Figure 12:
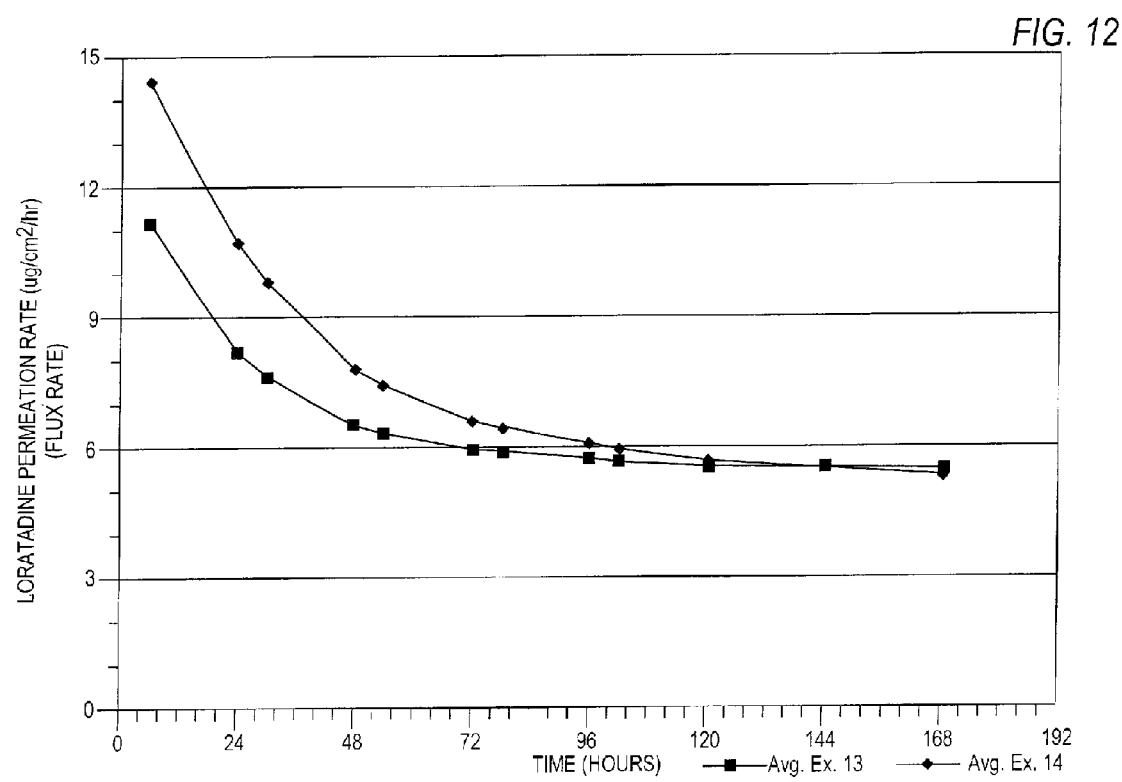
FIG. 12 is a graphical representation of the average loratadine permeation rates (flux rates) of Examples 13 and 14 through human cadaver skin.
Figure 13:
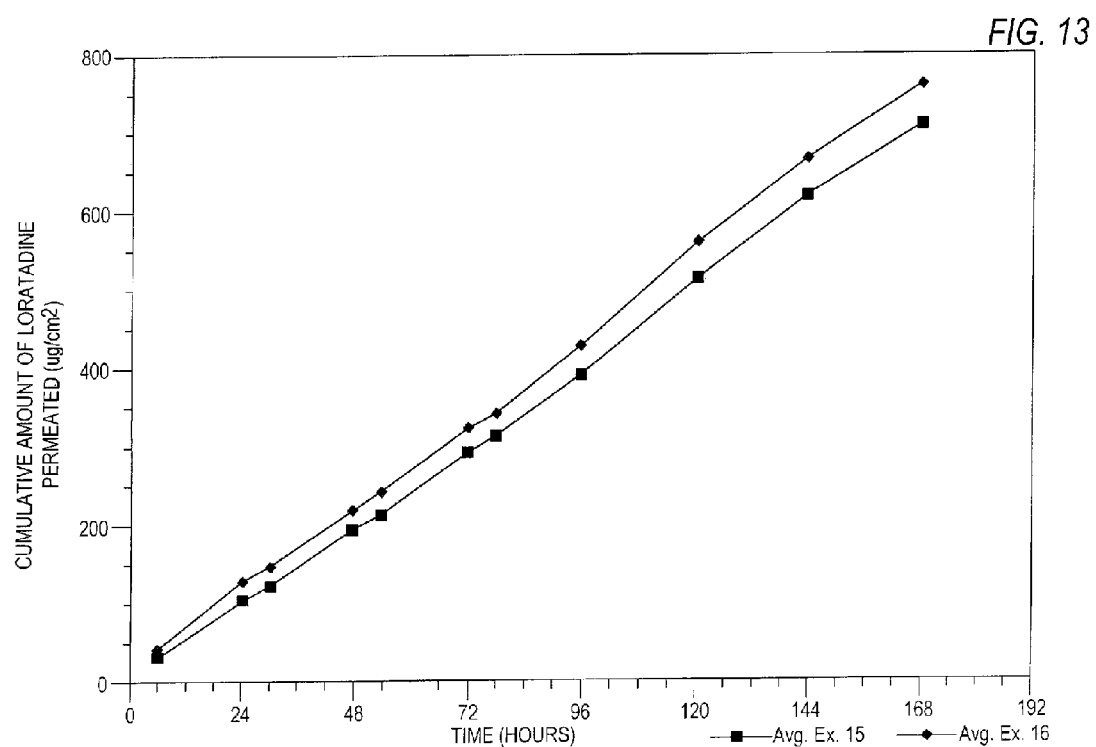
FIG. 13 is a graphical representation of the average cumulative amounts of loratadine resulting from permeation tests of Examples 15 and 16 through human cadaver skin.
Figure 14:
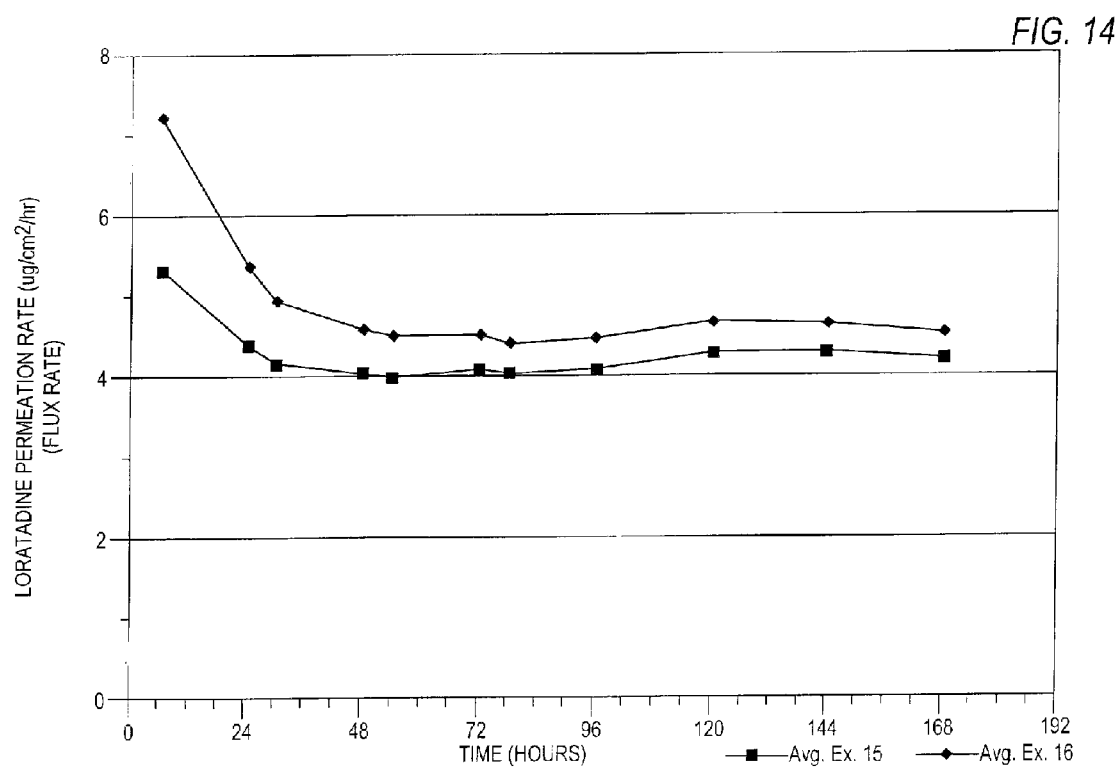
FIG. 14 is a graphical representation of the average loratadine permeation rates (flux rates) of Examples 15 and 16 through human cadaver skin.

Transdermal delivery of active agents is measured in terms of "relative release rate" or "flux", i.e., the rate of penetration of the active agent through the skin of an individual. Skin flux may be generally determined from the following equation:

$$dm/dT = J = P*C$$

where J is the skin flux, P is the permeability coefficient and C is the concentration gradient across the membrane, assumed to be the same as the donor concentration. M represents the amount of drug entering the blood stream. The variable dm/dT represents the change in the amount of drug entering the blood stream over time.

It is well understood in the art of transdermal delivery systems that in order to maintain a desired flux rate for a desired dosing period, it is necessary to include an overage of active agent in the transdermal delivery system in an amount that is substantially greater than the amount to be delivered to the patient over the desired time period. For example, to maintain the desired flux rate for a three day time period, it is considered necessary to include much greater than 100% of a three-day dose of an active agent in a transdermal delivery system. This overage is necessary for creating a concentration gradient by means of which the active agent migrates through the layers of the transdermal delivery system to the desired site on a patient's skin. The remainder of the active agent remains in the transdermal delivery system. It is only the portion of active agent that exits the transdermal delivery system that becomes available for absorption into the skin. The total amount of active agent absorbed into the patient's blood stream is less than the total amount available. The amount of overage to be included in a transdermal delivery system is dependent on these and other factors known to the skilled artisan.

It has been found that it is possible to treat seasonal allergic rhinitis and chronic idiopathic urticaria according to the present invention by providing a transdermal delivery system containing a sufficient amount of loratadine to provide a desired relative release rate for at least about 3 days, and after single administration (application) of the transdermal dosage form, leaving the dosage form on the skin for approximately a 3 to 8 day time period, thereby resulting in the flux being maintained over the prolonged period and effective blood plasma levels and management of seasonal allergic rhinitis or chronic idiopathic urticaria being maintained over the prolonged period. Preferably, the desired flux is maintained at least about 5, preferably at least about 7 days after application of the transdermal delivery system.

Transdermal dosage forms used in accordance with the invention preferably include a backing layer made of pharmaceutically acceptable material which is impermeable to loratadine. The backing layer preferably serves as a protective cover for the active agent, e.g. loratadine and may also provide a support function. Examples of materials suitable for making the backing layer are films of high and low density polyethylene, polypropylene, polyvinylchloride, polyurethane, polyesters such as poly(ethylene terephthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

Matrix Systems

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylene vinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable crosslinking agents include, e.g., tetrapropoxy silane.

Preferred transdermal delivery systems used in accordance with the methods of the present invention include an adhesive layer to affix the dosage form to the skin of the patient for a desired period of administration, e.g., about 3 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g, surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer preferably includes using any adhesive known in the art that is pharmaceutically compatible with the dosage form and preferably hypoallergenic, such as polyacrylic adhesive polymers, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the loratadine into the blood stream of the patient. A non-limiting list of permeation enhancing agents includes polyethylene glycols, surfactants, and the like.

Alternatively, permeation of loratadine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal dosage form. Other means of enhancing permeation of loratadine such as the use of iontophoretic means are also contemplated to be within the scope of the present invention.

A preferred transdermal dosage form which may be used in accordance with the present invention includes a non-permeable backing layer made, for example, of polyester; an adhesive layer made, for example of a polyacrylate; and a matrix containing the loratadine and other desirable pharmaceutical aids such as softeners, permeability enhancers, viscosity agents and the like.

The active agent may be included in the device in a drug reservoir, drug matrix or drug/adhesive layer. Preferably, the active agent is loratadine or a pharmaceutically acceptable salt thereof.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol which can also be etherified by polyethylene glycols.

A loratadine solvent may also be included in the transdermal delivery systems of the present invention. Preferably, the solvents dissolve the loratadine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polyltetra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage forms used in accordance with the invention and the type of device used are not considered critical to the method of the invention, provided that the device delivers the active agent, e.g. loratadine, for the desired time period and at the desired flux rate and/or the desired delivery rate of the transdermal dosage form.

Certain transdermal dosage forms for use in accordance with the present invention are described in U.S. Pat. No. 5,240,711 (Hille, et. al.; assigned to LTS Lohmann Therapie-Systeme GmbH & Co.), hereby incorporated by reference. Such transdermal delivery systems may be a laminated composite having an impermeable backing layer containing loratadine, e.g., instead of buprenorphine, and optionally a permeation enhancer combined with a pressure-sensitive adhesive. A preferred transdermal dosage form in accordance with the '711 patent includes: (i) a polyester backing layer which is impermeable to the drug; (ii) a polyacrylate adhesive layer; (iii) a separating polyester layer; and (iv) a matrix containing loratadine, a solvent for the loratadine, a softener and a polyacrylate adhesive. The loratadine solvent may or may not be present in the final formulation. The transdermal delivery device described therein includes a backing layer which is impermeable to the active substance, a pressure-sensitive adhesive reservoir layer and optionally, a removable protective layer. Preferably, the reservoir layer includes about 10 to about 95%-wt polymeric material, about 0.1 to about 40%-wt softener, about 0.1 to about 30%-wt loratadine. A solvent for the loratadine base or pharmaceutically acceptable salt thereof may be included as about 0.1 to about 30%-wt.

The transdermal delivery system may also be prepared in accordance with the disclosure of International Patent Application No. WO 96/19975 (Hille, et. al.; assigned to LTS Lohmann Therapie-Systeme GMBH), hereby incorporated by reference, where loratadine is substituted for buprenorphine as an active agent. In this device, the loratadine transdermal delivery device contains resorption-promoting auxiliary substances. The resorption-promoting auxiliary substance forms an undercooled mass. The delivery system contains 10% loratadine base, 10-15% acid (such as levulinic acid), about 10% softener (such as oleyoleate); 55-70% polyacrylate; and 0-10% polyvinylpyrollidone (PVP).

Reservoir Devices

Alternatively, the transdermal device may be a reservoir system. A reservoir system transdermal drug delivery patch comprises several different components. An exemplary construction includes a backing layer, an active drug and optional permeation enhancing solvent gel, a membrane, a skin contact adhesive layer, and a protective release coated liner film. Characteristics of each component are set forth below:

Backing Film: This layer is exposed to the external environment when the system is worn on the skin surface. It is impervious to penetration of the active drug contained within the system preventing the escape of the active drug through the backing film. The backing film serves as barrier layer. Moisture, soaps, lotions and other elements are prevented from entering the system and diluting the active ingredients or altering the release characteristics of the system. The active drug and solvent are contained within the system to perform its designated function. The backing film also forms one half of the chamber which contains the active drug reservoir. The backing film must be capable of being suitably attached to the membrane in order to form the reservoir chamber. Typical attachment methods include thermal, ultrasonic polymer heat seal or welding, and adhesive bonding. Necessary mechanical properties include a low compliance for conformability to the skin surface and elasticity to allow for movement with the skin surface. Typical thickness is in the range of 0.5-25.0 mil. A wide range of homogenous, woven, and non-woven polymer or composite materials are suitable as backing films.

Membrane: The membrane in combination with the backing film forms the chamber which contains the active drug reservoir. The membrane is attached to the backing film, and provides a support surface for the skin contact adhesive. The membrane can be a homogenous polymer film, or a material with a porous structure. The membrane may also be designed to control the transport rate of the active drug and/or the permeation enhancing solvent. Necessary mechanical properties include a low compliance for conformability to the skin surface and elasticity to allow for movement with the skin surface. Typical thickness is in the range of 0.25-30.0 mil and more preferably in the range of 0.5 to 25.0 mils. A wide range of homogenous, porous, woven, and non-woven polymer or composite materials are suitable as membranes and known in the art.

Active Drug Reservoir: The active drug is combined with a liquid vehicle to fill the reservoir chamber. A range of solvents can be used for the liquid vehicle. The solvents can be chosen to optimize skin permeation of the active (enhancers) or to optimize the permeation characteristics of the membrane or the adhesion of the skin contact adhesive. A viscosity increasing agent is often included in the vehicle to aid in the handling and system manufacturing process. The composition of the vehicle must be compatible with the other components of the system. The vehicle may be in the form of a solution, suspension, cream, lotion, gel, physical mixture or emulsion. This list is not meant to be exhaustive.

Skin Contact Adhesive: The system is affixed to the skin with a skin contact adhesive. The adhesive may cover the entire surface of the system membrane, be applied in an intermittent pattern, or only to the perimeter of the system. The adhesive composition must be of materials suitable for skin contact without creating intolerable adverse effects such as excessive skin irritation or sensitization. Adequate adhesion to the membrane and skin are also necessary. The adhesive must also possess enough cohesive integrity to remain completely on the membrane upon removal of the system. The adhesive is applied in a thickness to provide a weight of 0.025 to 50.0 mg/cm$^2$, more preferably 0.25 to 1.0 mg/cm$^2$ and most preferably 0.3 to 0.6 mg/cm$^2$. Typical materials include silicone, polyisobutylene (PIB), and acrylates dissolved in organic solvents, aqueous emulsions, or directly applied by hot melt processing.

Release Coated Liner Film: The liner film is removed from the system before application to the skin surface. The liner film serves the function as a protective barrier to the skin contact adhesive prior to use. The coating on the liner provides a release capability for the adhesive, allowing separation of the liner from the adhesive. A coating is not necessary if the liner material is readily removed from the adhesive without disrupting the reservoir system. Typical thickness is in the range of 0.5-25.0 mil. A wide range of homogenous, woven, and non-woven paper, polymer or composite materials are suitable as liner films. Release coatings are typically composed of paraffin, polyethylene, silicone or fluorocarbons.

In other embodiments, the transdermal delivery system may be a plaster such as that described in U.S. Pat. No. 5,225,199 to Hidaka et al., hereby incorporated by reference. Such plasters include a film layer including a polyester film of about 0.5 to about 4.9 µm thickness, about 8 to about 85 g/mm strength, respectively in the two directions intersecting substantially at right angles, about 30 to about 150% elongation, in the two directions intersecting substantially at right angles and an elongation ratio of A to B of about 1:0 to about 5.0, wherein A and B represent data in two directions intersecting at right angles, and A is greater than B and wherein the polyester film includes about 0.01 to about 1.0% by weight, based on the total weight of the polyester film, of solid fine particles in which the average particle size is about 0.001 to about 3.0 µm and an adhesive layer which is composed of an adhesive containing transdermally absorbable drugs; wherein the adhesive layer is laminated on the film layer over the surface in about 2 to about 60 µm thickness. The average particle size is substantially not more than 1.5 times the thickness of the polyester film.

The transdermal delivery system used in the present invention may also be prepared in accordance with U.S. Pat. No. 5,879,701, issued Mar. 9, 1999 to Audett, et al., hereby incorporated by reference, wherein solubilization enhancer compositions are provided which facilitate transdermal administration of basic drugs from transdermal systems composed of nonpolar adhesive materials. The solubilization enhancing composition is particularly useful in facilitating the administration of basic drugs using transdermal systems worn for at least four days containing drug reservoirs comprised of nonpolar materials such as polyisobutylene adhesives or the like. The solubilizing enhancing composition itself is preferably a liquid which is an isomeric acid mixture. Examples of suitable solubilizers include, but are not limited to, oleic acid dimer and neodecanoic acid, with oleic acid dimer particularly preferred. The solubilizer constitutes at least about 0.10 wt. % of the reservoir, and preferably represents on the order of 0.25 wt. % to 1.0 wt. % of the reservoir. The amount of enhancer composition present in the drug formulation will depend on a number of factors, e.g., the strength of the particular enhancer composition, the desired increase in skin permeability, and the amount of drug which is necessary to deliver.

The adult oral dosage for loratadine is 10 mg/day. The bioavailability for the drug is 20%, expressed as fraction, 0.20 of the oral dose made available to the blood stream from gastrointestinal absorption. A release rate for a loratadine transdermal delivery system was calculated from this data. 0.20 of the oral 10 mg daily dose provides 2.0 mg of loratadine available into the blood stream. Therefore, an equal dose is required to be delivered transdermally. 2.0 mg/day is converted to 2000 mcg/24 hours. This would require delivery of 83.3 mcg/hour. The largest desirable surface area for a transdermal patch is about 40 cm$^2$. Dividing 83.3 mcg/hour/40 cm$^2$ by 40, yields a release rate of 2.1 mcg/hour/cm$^2$ of transdermal patch surface area. To account for drug elimination, further pharmacokinetic data and physiological data was required. The plasma concentration at steady state for loratadine is 0.002 mcg/ml. The physiological clearance rate is 196,000 ml/hour. The dosing rate is obtained from the product of the steady state concentration of loratadine and a representative clearance rate. This product is 392 mcg/hour. The largest desirable surface area for a transdermal patch is about 40 cm$^2$. Dividing 392 mcg/hour/40 cm$^2$ by 40, yields a release rate of 9.8 mcg/hour/cm$^2$ of transdermal patch surface area. One of skill would expect a larger input rate or flux to maintain a steady state concentration in consideration of the loss of drug in the plasma due to elimination. A confirmatory calculation for flux requires further pharmacokinetic parameters. The volume of distribution for loratadine is 1,660,000 ml and the half-life is 8.4 hours. The elimination rate constant is 0.693/half-life. The product of steady state concentration, volume of distribution and elimination rate constant yields a rate of 274 mcg/hour. The largest desirable surface area for a transdermal patch is about 40 cm$^2$. Dividing 274 mcg/hour/40 cm$^2$ by 40, yields a release rate of 6.85 mcg/hour/cm$^2$ of transdermal patch surface area.

Any type of transdermal delivery system may be used in accordance with the methods of the present invention so long as the desired pharmacokinetic and pharmacodynamic response(s) are attained over at least 3 days, e.g., from about 5 to about 8 days. Preferable transdermal delivery systems include e.g., transdermal patches, transdermal plasters, transdermal discs, iontophoretic transdermal devices and the like.

DETAILED DESCRIPTION OF THE PREFERRED EMBODIMENTS

The following examples illustrate various aspects of the present invention. They are not to be construed to limit the claims in any manner whatsoever.

Overview of Method of Manufacture: Matrix System

The following general method is used in the following examples in which the transdermal device tested is a matrix system (device):

Step 1: Preparation of the active drug vehicle/solvent/adhesive matrix. Active drug is combined with the liquid vehicle components and the adhesive components using appropriate mixing techniques well known in the art. Simple mechanical mixers, motionless mixers, homogenizers, high shear mixers, and magnetic mixing devices can be employed.

Step 2: Preparation of the active drug/adhesive matrix coated liner. Active drug/adhesive matrix coating is done with continuous web based equipment on a commercial scale. Small sheet batches can be made readily in the lab manually. A mechanism for applying a controlled thickness coating of the active drug/adhesive matrix onto the liner is employed. If solvent-based adhesives are used, a procedure for driving off the solvent and drying the active drug/adhesive matrix is employed. The open surface of the active drug/adhesive matrix on the liner must be protected during processing. A second intermediate liner can be used to cover this active drug/adhesive matrix surface.

Step 3: Laminating of the membrane to active drug/adhesive and/or liner. The membrane is typically applied on line after solvent removal on a commercial scale. This avoids the need for a second liner. A separate web and a heat and/or pressure lamination station bonds the two layers. The membrane provides a non-stick surface to the open side of the adhesive and allows for further processing in a roll form.

Overview of the Manufacture of Reservoir Devices

The following general method is used in the following examples in which the transdermal device tested is a reservoir system (device):

Step 1: Preparation of the adhesive coated liner. Adhesive coating is done with continuous web based equipment on a commercial scale. Small sheet batches can be made readily in the lab manually. A mechanism for applying a controlled thickness coating of the adhesive onto the liner is employed. If solvent-based adhesives are used, a procedure for driving off the solvent and drying the adhesive is employed. The open surface of the adhesive on the liner must be protected during processing. A second intermediate liner can be used to cover this adhesive surface.

Step 2: Laminating of the membrane to adhesive and/or liner. The membrane is typically applied on line after solvent removal on a commercial scale. This avoids the need for a second liner. A separate web and a heat and/or pressure lamination station bonds the two layers. The membrane provides a non-stick surface to the open side of the adhesive and allows for further processing in a roll form.

Step 3: Preparation of the active vehicle/solvent combination. Active drug is combined with the liquid vehicle components using appropriate mixing techniques well known in the art. Simple mechanical mixers, motionless mixers, homogenizers, high shear mixers, and magnetic mixing devices can be employed. Other ingredients are also incorporated at this time. These may include permeation enhancers and viscosity thickeners, for example.

Step 4: Finalizing the delivery system utilizing the form, fill and seal process incorporating the reservoir and backing film. This process can be carried out in either a horizontal or vertical plane. The horizontal mode requires a thickened viscosity of the reservoir vehicle, while the vertical mode can handle liquid vehicles of minimal viscosity. In the horizontal mode a dispensing head places a fixed volume drop of the drug vehicle onto the surface of the membrane. The backing film is then placed over the drop of vehicle, and then bound to the membrane to enclose the active/vehicle. A heated die is commonly used to form a heat seal welded bond. In web based systems a die cutting and packaging station often follows.

In-vitro Skin Permeation Test Method

The test methods utilized in the following examples involves the use of a permeation cell. Several permeation cell designs are available for in-vitro permeation testing. These include "Franz cells", "Valia-Chien cells", and "Bronaugh cells". Each cell design shares several common characteristics. All cells are made with a definable surface area for permeation. All cells contain two chambers and a clamping mechanism to hold the test membrane positioned between the two cell chambers. Several exemplary test membranes include mouse skin and human cadaver skin. The membrane may be oriented in either the horizontal or vertical plane based on the cell special arrangement. One chamber serves as a reservoir (donor) for the drug to be tested, the second is a place where the permeated drug is accumulated (receptor). The receptor is often chosen to mimic the physiological conditions found beneath the membrane in-vivo. In the case where a complete transdermal system is the donor, it is clamped between the two chambers and only the receptor chamber is filled.

Calculation of the permeation rate (J) requires knowledge of the concentration (C) of the drug in the receptor chamber, the permeation area (A), sampling interval (t) and the receptor volume (V). The equation below is typical:

$J = CV/At$ where:
$J = micrograms/cm^2\text{-}hr$
$C = micrograms/ml$
$V = ml$
$A = cm^2$
$t = hr$ Only the drug concentration and testing time vary in typical experiments. The drug concentration is determined by any appropriate analytical technique such as high performance liquid chromatograpy, gas chromatograpy, or ultraviolet spectrophotometry. Other considerations in the testing system may include temperature control systems, receptor stirring systems, flow through receptor chambers, and automated sampling equipment utilizing pumps and fraction collectors. Partial receptor sampling protocols have been used in situations where the sensitivity of the analytical method for determining the drug concentration was less than optimal.

Sample Testing Protocols for Loratadine Follow.

| | |
|---|---|
| Cells | Valia Chien |
| Membrane | Human cadaver skin |
| A (cm2) | 0.636 |
| V (ml) | 4.0 |
| receptor | Ethanol/water 40/60 |
| sampling points | 6, 24, 48, 72, 120, 144, 168 hours |
| sampling mode: | partial, 0.6 ml per point, replace with fresh receptor. |

HPLC Conditions for Determination of Drug Concentration

| | |
|---|---|
| Column | Altima C8, 5 um, 4.6 mm × 15 cm |
| Mobile phase | Acetonitrile/Buffer 70/30 |
| Buffer: | 0.01M phosphate at pH 4.5 |
| Flow rate | 1 ml/min |
| UV detection | 205 nm |
| Injection volume | 20 microliters |
| Retention time | 5.0 minutes |

EXAMPLE 1

A Loratadine drug reservoir formulation was prepared having the formulation set forth in Table 1A below:

TABLE 1A

| Ingredient | Amount (gm) |
|---|---|
| Loratadine | 0.5 |
| Ethanol | 12.2 |
| Water | 15 |
| Total | 27.7 |
| Ethylvinylacetate membrane | |

The formulation of Table 1A was prepared and incorporated into a permeation testing apparatus according to the following procedure:

1. Loratadine is dissolved with ethanol and water and the solution is placed into the donor cell.
2. The ethylvinylacetate membrane is placed against the donor cell.
3. Thereafter, the human cadaver skin is placed between the membrane and the receptor cell and the apparatus is secured.

The formulation of Example 1 was tested using a permeation cell with a definable surface area for permeation. The receptor of the permeation cell was Ethanol:water (40:60). Three permeation tests (1-1, 1-2, 1-3) were conducted giving the results listed in Table 1B below:

TABLE 1B

| Test # | Sampling Time (Hours) | Drug Conc. (μg/ml) | Receptor Volume (ml) | Drug amount (μg) | Sampling Volume (ml) | Drug Loss due to Sampling (μg) | Cumulative Drug Loss (μg) | Cumulative Amount Permeated (μg) | Amount Permeated per cm² (μg/cm²) |
|---|---|---|---|---|---|---|---|---|---|
| 1-1 | 1 | 0.000 | 4 | 0.000 | 4 | 0.000 | 0.000 | 0.000 | 0.000 |
| | 2 | 0.177 | 4 | 0.708 | 4 | 0.708 | 0.000 | 0.708 | 1.113 |
| | 16 | 14.449 | 4 | 57.796 | 4 | 57.796 | 0.708 | 58.504 | 91.959 |
| | 17 | 0.914 | 4 | 3.656 | 4 | 3.656 | 58.504 | 62.160 | 97.705 |
| | 24 | 6.666 | 4 | 26.664 | 4 | 26.664 | 62.160 | 88.824 | 139.616 |
| | 42 | 18.644 | 4 | 74.576 | 4 | 74.576 | 88.824 | 163.400 | 256.837 |
| | 48 | 6.639 | 4 | 26.556 | 4 | 26.556 | 163.400 | 189.956 | 298.579 |
| | 168 | 120.233 | 4 | 480.932 | 4 | 480.932 | 189.956 | 670.888 | 1054.524 |
| 1-2 | 1 | 0.000 | 4 | 0.000 | 4 | 0.000 | 0.000 | 0.000 | 0.000 |
| | 2 | 0.154 | 4 | 0.616 | 4 | 0.616 | 0.000 | 0.616 | 0.968 |
| | 16 | 11.703 | 4 | 46.812 | 4 | 46.812 | 0.616 | 41.428 | 74.549 |
| | 17 | 0.433 | 4 | 1.732 | 4 | 1.732 | 47.428 | 49.160 | 77.271 |
| | 24 | 5.388 | 4 | 21.552 | 4 | 21.552 | 49.160 | 70.712 | 111.147 |
| | 42 | 15.636 | 4 | 62.544 | 4 | 62.544 | 70.712 | 133.256 | 209.456 |
| | 48 | 5.223 | 4 | 20.892 | 4 | 20.892 | 133.256 | 154.148 | 242.295 |
| | 168 | 113.298 | 4 | 453.192 | 4 | 453.192 | 154.148 | 607.340 | 945.637 |
| 1-3 | 1 | 0.000 | 4 | 0.000 | 4 | 0.000 | 0.000 | 0.000 | 0.000 |
| | 2 | 0.019 | 4 | 0.076 | 4 | 0.076 | 0.000 | 0.076 | 0.119 |
| | 16 | 10.734 | 4 | 42.936 | 4 | 42.936 | 0.076 | 43.012 | 67.608 |
| | 17 | 0.547 | 4 | 2.188 | 4 | 2.188 | 43.012 | 45.200 | 71.047 |
| | 24 | 4.741 | 4 | 18.964 | 4 | 18.964 | 45.200 | 64.064 | 100.855 |
| | 42 | 15.189 | 4 | 60.756 | 4 | 60.756 | 64.164 | 124.920 | 196.353 |
| | 48 | 4.950 | 4 | 19.800 | 4 | 19.800 | 124.920 | 144.720 | 227.476 |
| | 168 | 107.974 | 4 | 431.896 | 4 | 431.896 | 144.720 | 576.616 | 906.344 |

Based on the permeation results of Example 1, listed in Table 1B, the averages of the three calculated and the flux results listed in Table 1C below were obtained:

TABLE 1C

| Hours | Test 1-1 | Test 1-2 | Test 1-3 | Avg. of all 3 tests | Std Dev | μg/cm²/hr |
|---|---|---|---|---|---|---|
| 1 | 0.000 | 0.000 | 0.000 | 0.000 | 0.000 | 0.000 |
| 2 | 1.113 | 0.968 | 0.119 | 0.733 | 0.537 | 0.367 |
| 16 | 91.959 | 74.549 | 67.608 | 78.039 | 12.545 | 4.877 |
| 17 | 97.705 | 77.271 | 71.047 | 82.008 | 13.946 | 4.824 |
| 24 | 139.616 | 111.147 | 100.855 | 117.206 | 20.078 | 4.884 |
| 42 | 256.837 | 209.456 | 196.353 | 220.882 | 31.820 | 5.259 |
| 48 | 298.579 | 242.295 | 227.476 | 256.117 | 37.513 | 5.336 |
| 168 | 1054.524 | 954.637 | 906.344 | 971.835 | 75.572 | 5.785 |
| $F_{4-76}$ | 6.435 | 5.245 | 4.957 | 5.546 | 0.784 | |
| CORR | 1.000 | 1.000 | 0.999 | 1.000 | | |

EXAMPLE 2

A Loratadine reservoir and adhesive formulation was prepared having the formulation set forth in Table 2A below:

TABLE 2A

| Ingredient | Amount (gm) |
|---|---|
| Loratadine | 1.0 |
| Ethanol | 22.0 |
| Water | 27.0 |
| Total | 50.0 |
| Polyethylene membrane | |
| Silicone adhesive | |

The formulation of Table 2A was prepared and incorporated into a permeation testing apparatus according to the following procedure:

1. Loratadine is dissolved with ethanol and water and the solution is placed into the donor cell.
2. The polyethylene membrane is coated with a silicone adhesive and placed against the donor cell. The adhesive coated membrane is positioned opposite from the donor cell.
3. Thereafter, the human cadaver skin is placed between the adhesive coated polyethylene membrane and the receptor cell and the apparatus is secured.

The formulation of Example 2 was tested using a permeation cell with a definable surface area for permeation. The receptor of the permeation cell was Ethanol:water (40:60). Three permeation tests (2-1, 2-2, 2-3) were conducted giving the results listed in Table 2B below:

TABLE 2B

| | μg/cm² | | | | | |
|---|---|---|---|---|---|---|
| Hours | Test 2-1 | Test 2-2 | Test 2-3 | Test 2-4 | Avg. of all 4 tests | Std Dev |
| 6 | 5.608 | 7.362 | 6.344 | 4.231 | 5.886 | 1.317 |
| 24 | 87.325 | 83.930 | 66.665 | 66.771 | 76.173 | 11.005 |
| 30 | 125.489 | 120.132 | 91.229 | 92.763 | 107.406 | 17.936 |
| 48 | 228.840 | 220.207 | 158.202 | 165.954 | 193.307 | 36.363 |
| 54 | 271.600 | 262.829 | 183.313 | 193.688 | 227.858 | 45.783 |
| 72 | 381.257 | 368.375 | 249.607 | 269.632 | 317.218 | 67.215 |
| 78 | 425.099 | 409.871 | 273.618 | 297.447 | 351.509 | 77.053 |
| 96 | 544.508 | 521.226 | 343.427 | 375.668 | 446.207 | 101.375 |
| 102 | 592.644 | 565.193 | 368.375 | 404.470 | 482.671 | 112.669 |
| 120 | 715.385 | 675.064 | 436.674 | 483.691 | 577.704 | 138.037 |

TABLE 2B-continued

μg/cm$^2$

| Hours | Test 2-1 | Test 2-2 | Test 2-3 | Test 2-4 | Avg. of all 4 tests | Std Dev |
|---|---|---|---|---|---|---|
| 144 | 892.983 | 836.158 | 536.473 | 598.510 | 716.031 | 174.924 |
| 168 | 1046.419 | 982.364 | 627.249 | 701.572 | 839.401 | 205.994 |

Based on the permeation results of Example 2, listed in Table 2B, the following flux results listed in Table 2C below were obtained:

TABLE 2C

μg/cm$^2$/hr

| Hours | Test 2-1 | Test 2-2 | Test 2-3 | Test 2-4 | Avg. of all 4 tests | Std Dev |
|---|---|---|---|---|---|---|
| 6 | 0.935 | 1.224 | 1.057 | 0.705 | 0.981 | 0.220 |
| 24 | 3.639 | 3.497 | 2.778 | 2.782 | 3.174 | 0.459 |
| 30 | 4.183 | 4.004 | 3.041 | 3.092 | 3.580 | 0.598 |
| 48 | 4.768 | 4.588 | 3.296 | 3.457 | 4.027 | 0.758 |
| 54 | 5.030 | 4.867 | 3.395 | 3.587 | 4.220 | 0.848 |
| 72 | 5.295 | 5.116 | 3.467 | 3.745 | 4.406 | 0.934 |
| 78 | 5.450 | 5.255 | 3.508 | 3.813 | 4.507 | 0.988 |
| 96 | 5.672 | 5.429 | 3.577 | 3.913 | 4.648 | 1.056 |
| 102 | 5.810 | 5.541 | 3.612 | 3.965 | 4.732 | 1.105 |
| 120 | 5.962 | 5.626 | 3.639 | 4.031 | 4.814 | 1.150 |
| 144 | 6.201 | 5.807 | 3.726 | 4.156 | 4.972 | 1.215 |
| 168 | 6.229 | 5.847 | 3.734 | 4.176 | 4.996 | 1.226 |
| $F_{6-96}$ | 6.066 | 5.815 | 3.770 | 4.173 | 4.956 | 1.153 |
| CORR | 0.998 | 0.998 | 1.000 | 0.999 | 0.999 | |

EXAMPLE 3

A Loratadine active drug/adhesive matrix formulation was prepared having the formulation set forth in Table 3A below:

TABLE 3A

| Ingredient | Amount (gm) |
|---|---|
| Loratadine | 0.23 |
| Ethyl Acetate | 1.77 |
| BIO PSA 7-4302 (adhesive solution) containing 9.8 gm silicone adhesive (60% solids) | 16.3 |
| Total | 18.3 |

The formulation of Table 3A was prepared and incorporated into a permeation testing apparatus according to the following procedure:

1. Loratadine is dispersed in the requisite amount of ethyl acetate and adhesive solution to form the active drug/adhesive matrix.
2. The active drug/adhesive matrix is applied to a backing layer and dried.
3. Thereafter, the patch is applied to the human cadaver skin affixed to the receptor cell.

The formulation of Example 3 was tested using a permeation cell with a definable surface area for permeation. The receptor of the permeation cell was ethanol:water (40:60) and the membrane was a human cadaver skin membrane. Three permeation tests (3-1, 3-2, 3-3) were conducted giving the results listed in Table 3B below:

TABLE 3B

| Test # | Sampling Time (Hours) | Drug Conc. (μg/ml) | Receptor Volume (ml) | Drug amount (μg) | Sampling Volume (ml) | Drug Loss due to Sampling (μg) | Cumulative Drug Loss (μg) | Cumulative Amount Permeated (μg) | Amount Permeated per cm$^2$ (μg/cm$^2$) |
|---|---|---|---|---|---|---|---|---|---|
| 3-1 | 4 | 3.220 | 13 | 41.860 | 1 | 3.220 | 0.000 | 41.860 | 23.690 |
| | 24 | 34.978 | 13 | 454.714 | 1 | 34.978 | 3.220 | 457.934 | 259.159 |
| | 28 | 35.903 | 13 | 466.739 | 1 | 35.903 | 38.198 | 504.937 | 285.759 |
| | 48 | 55.584 | 13 | 722.592 | 1 | 55.584 | 74.101 | 796.693 | 450.873 |
| | 52 | 49.609 | 13 | 644.917 | 1 | 49.609 | 129.685 | 774.602 | 438.371 |
| | 72 | 60.990 | 13 | 792.870 | 1 | 60.990 | 179.294 | 972.164 | 550.178 |
| | 76 | 54.504 | 13 | 708.552 | 1 | 54.504 | 240.284 | 948.836 | 536.976 |
| | 96 | 61.080 | 13 | 794.040 | 1 | 61.080 | 294.788 | 1088.828 | 616.201 |
| 3-2 | 4 | 4.782 | 13 | 62.166 | 1 | 4.782 | 0.000 | 62.166 | 35.182 |
| | 24 | 37.018 | 13 | 481.234 | 1 | 37.018 | 4.782 | 486.016 | 275.051 |
| | 28 | 38.489 | 13 | 500.357 | 1 | 38.489 | 41.800 | 542.157 | 306.823 |
| | 48 | 54.826 | 13 | 712.738 | 1 | 54.826 | 80.289 | 793.027 | 448.799 |
| | 52 | 54.818 | 13 | 712.634 | 1 | 54.818 | 135.115 | 847.749 | 479.767 |
| | 72 | 61.280 | 13 | 796.640 | 1 | 61.280 | 189.933 | 986.573 | 558.332 |
| | 76 | 59.295 | 13 | 770.835 | 1 | 59.295 | 251.213 | 1022.048 | 578.409 |
| | 96 | 60.455 | 13 | 785.915 | 1 | 60.455 | 310.508 | 1096.423 | 620.500 |
| 3-3 | 4 | 2.418 | 13 | 31.434 | 1 | 2.418 | 0.000 | 31.434 | 17.789 |
| | 24 | 30.875 | 13 | 401.375 | 1 | 30.875 | 2.418 | 403.793 | 228.519 |
| | 28 | 33.696 | 13 | 438.048 | 1 | 33.696 | 33.293 | 471.341 | 266.746 |
| | 48 | 51.182 | 13 | 665.366 | 1 | 51.182 | 66.989 | 732.355 | 414.462 |
| | 52 | 50.819 | 13 | 660.647 | 1 | 50.819 | 118.171 | 778.818 | 440.757 |
| | 72 | 59.651 | 13 | 775.463 | 1 | 59.651 | 168.990 | 944.453 | 534.495 |
| | 76 | 55.812 | 13 | 725.556 | 1 | 55.812 | 228.641 | 954.197 | 540.010 |
| | 96 | 63.094 | 13 | 820.222 | 1 | 63.094 | 284.453 | 1104.675 | 625.170 |

Based on the permeation results of Example 3, listed in Table 3B, the averages of all three calculated and the flux results listed in Table 3C below were obtained:

TABLE 3C

| Hours | Test 3-1 | Test 3-2 | Test 3-3 | Avg. of all 3 tests | Std Dev | $\mu g/cm^2/hr$ |
|---|---|---|---|---|---|---|
| 4 | 23.690 | 35.182 | 17.789 | 25.554 | 8.845 | 6.388 |
| 24 | 259.159 | 275.051 | 228.519 | 254.243 | 23.652 | 10.593 |
| 28 | 285.759 | 306.823 | 266.746 | 286.443 | 20.047 | 10.230 |
| 48 | 450.873 | 448.799 | 414.462 | 438.045 | 20.449 | 9.123 |
| 52 | 438.371 | 479.767 | 440.757 | 452.965 | 23.242 | 8.711 |
| 72 | 550.178 | 558.332 | 534.495 | 547.668 | 12.115 | 7.607 |
| 76 | 536.946 | 578.409 | 540.010 | 551.798 | 23.095 | 7.261 |
| 96 | 616.201 | 620.500 | 625.170 | 620.624 | 4.486 | 6.465 |
| $F_{4-76}$ | 6.917 | 7.120 | 7.069 | 7.036 | 0.015 | |
| CORR | 0.970 | 0.975 | 0.982 | 0.976 | | |

EXAMPLE 4

A Loratadine active drug/adhesive matrix formulation was prepared having the formulation set forth in Table 4A below:

TABLE 4A

| Ingredient | Amount (gm) |
|---|---|
| Loratadine | 0.23 |
| Ethyl Acetate | 1.77 |
| DURO-TAK 87-6430 (adhesive solution) containing 9.8 gm Polyisobutylene adhesive (30% solids) | 32.6 |
| Total | 34.6 |

The formulation of Table 4A was prepared and incorporated into a permeation testing apparatus according to the same procedure as in Example 3, using DURO-TAK 87-6430 as the adhesive solution.

the formulation of Example 4 was tested using a permeation cell with a definable surface area for permeation. The receptor of the permeation cell was ethanol:water (40:60). Three permeation tests (4-1, 4-2, 4-3) were conducted giving the results listed in Table 4B below:

TABLE 4B

| Test # | Sampling Time (Hours) | Drug Conc. ($\mu g/ml$) | Receptor Volume (ml) | Drug amount ($\mu g$) | Sampling Volume (ml) | Drug Loss due to Sampling ($\mu g$) | Cumulative Drug Loss ($\mu g$) | Cumulative Amount Permeated ($\mu g$) | Amount Permeated per $cm^2$ ($\mu g/cm^2$) |
|---|---|---|---|---|---|---|---|---|---|
| 4-1 | 4 | 0.750 | 13 | 9.750 | 1 | 0.750 | 0.000 | 9.750 | 5.518 |
| | 24 | 8.590 | 13 | 111.670 | 1 | 8.590 | 0.750 | 112.420 | 63.622 |
| | 28 | 9.430 | 13 | 122.590 | 1 | 9.430 | 9.340 | 131.930 | 74.663 |
| | 48 | 13.706 | 13 | 178.178 | 1 | 13.706 | 18.770 | 196.945 | 111.459 |
| | 52 | 12.916 | 13 | 167.908 | 1 | 12.916 | 32.476 | 200.384 | 113.404 |
| | 72 | 15.903 | 13 | 206.739 | 1 | 15.903 | 45.392 | 252.131 | 142.689 |
| | 76 | 15.470 | 13 | 201.110 | 1 | 15.470 | 61.295 | 262.405 | 148.503 |
| | 96 | 16.762 | 13 | 217.906 | 1 | 16.762 | 76.765 | 294.671 | 166.763 |
| 4-2 | 4 | 0.468 | 13 | 6.084 | 1 | 0.468 | 0.000 | 6.084 | 3.443 |
| | 24 | 8.485 | 13 | 110.305 | 1 | 8.485 | 0.468 | 110.773 | 62.690 |
| | 28 | 8.718 | 13 | 113.334 | 1 | 8.718 | 8.953 | 122.287 | 69.206 |
| | 48 | 12.944 | 13 | 168.272 | 1 | 12.944 | 17.671 | 185.943 | 105.231 |
| | 52 | 11.946 | 13 | 155.298 | 1 | 11.946 | 30.615 | 185.913 | 105.214 |
| | 72 | 15.568 | 13 | 202.384 | 1 | 15.568 | 42.561 | 244.945 | 138.622 |
| | 76 | 14.784 | 13 | 192.192 | 1 | 14.784 | 58.129 | 250.321 | 141.664 |
| | 96 | 16.423 | 13 | 213.499 | 1 | 16.423 | 72.913 | 286.412 | 162.089 |
| 4-3 | 4 | 0.660 | 13 | 8.580 | 1 | 0.660 | 0.000 | 8.580 | 4.856 |
| | 24 | 9.734 | 13 | 126.542 | 1 | 9.734 | 0.660 | 127.202 | 71.988 |
| | 28 | 9.973 | 13 | 129.649 | 1 | 9.973 | 10.394 | 140.043 | 79.255 |
| | 48 | 14.864 | 13 | 193.232 | 1 | 14.864 | 20.367 | 213.599 | 120.882 |
| | 52 | 13.830 | 13 | 179.790 | 1 | 13.830 | 35.231 | 215.021 | 121.687 |
| | 72 | 17.243 | 13 | 224.159 | 1 | 17.243 | 49.061 | 273.220 | 154.624 |
| | 76 | 16.208 | 13 | 210.704 | 1 | 16.208 | 66.304 | 277.008 | 156.767 |
| | 96 | 18.495 | 13 | 240.435 | 1 | 18.495 | 82.512 | 322.947 | 182.766 |

Based on the permeation results of Example 4, listed in Table 4B, the averages of all three test were calculated and the flux results listed in Table 4C below were obtained:

TABLE 4C

| Hours | Test 4-1 | Test 4-2 | Test 4-3 | Avg. of all 3 tests | Std Dev | µg/cm²/hr |
|---|---|---|---|---|---|---|
| 4 | 5.518 | 3.443 | 4.856 | 4.606 | 1.060 | 1.151 |
| 24 | 63.622 | 62.690 | 71.988 | 66.100 | 5.120 | 2.754 |
| 28 | 74.663 | 69.206 | 79.255 | 74.375 | 5.031 | 2.656 |
| 48 | 111.459 | 105.231 | 120.882 | 112.524 | 7.880 | 2.344 |
| 52 | 113.404 | 105.214 | 121.687 | 113.435 | 8.237 | 2.181 |
| 72 | 142.689 | 138.622 | 154.624 | 145.312 | 8.317 | 2.018 |
| 76 | 148.503 | 141.664 | 156.767 | 148.978 | 7.563 | 1.960 |
| 96 | 166.763 | 162.089 | 182.766 | 170.539 | 10.843 | 1.776 |
| $F_{4-76}$ | 1.881 | 1.820 | 2.006 | 1.902 | 0.095 | |
| CORR | 0.983 | 0.984 | 0.979 | 0.982 | | |

EXAMPLE 5

A Loratadine active drug/adhesive matrix formulation was prepared having the formulation set forth in Table 5A below:

TABLE 5A

| Ingredient | Amount (gm) |
|---|---|
| Loratadine | 0.23 |
| Ethyl Acetate | 1.77 |
| DURO-TAK 87-8298 (adhesive solution) containing 9.8 gm acrylate adhesive (38.5% solids) | 28.8 |
| Total | 30.8 |

The formulation of Table 5A was prepared and incorporated into a permeation testing apparatus according to the same procedure as in Example 3, using DURO-TAK 87-8298 as the adhesive solution.

The formulation of Example 5 was tested using a permeation cell with a definable surface area for permeation. The receptor of the permeation cell was Ethanol:water (40:60). Two permeation tests (5-1, 5-2) were conducted giving the results listed in Table 5B below:

TABLE 5B

| Test # | Sampling Time (Hours) | Drug Conc. (µg/ml) | Receptor Volume (ml) | Drug amount (µg) | Sampling Volume (ml) | Drug Loss due to Sampling (µg) | Cumulative Drug Loss (µg) | Cumulative Amount Permeated (µg) | Amount Permeated per cm² (µg/cm²) |
|---|---|---|---|---|---|---|---|---|---|
| 5-1 | 6 | 1.828 | 12 | 21.936 | 1 | 1.828 | 0.000 | 21.936 | 12.414 |
|  | 24 | 11.188 | 12 | 134.256 | 1 | 11.188 | 1.828 | 136.08 | 77.014 |
|  | 48 | 22.197 | 12 | 266.364 | 1 | 22.197 | 13.016 | 279.38 | 157.110 |
|  | 72 | 30.850 | 12 | 370.200 | 1 | 30.850 | 35.213 | 405.41 | 229.436 |
|  | 96 | 36.048 | 12 | 432.576 | 1 | 36.048 | 66.063 | 498.64 | 282.195 |
|  | 120 | 39.128 | 12 | 469.536 | 1 | 39.128 | 102.111 | 571.65 | 323.513 |
|  | 148 | 39.190 | 12 | 470.280 | 1 | 39.190 | 141.239 | 611.52 | 346.078 |
|  | 168 | 39.347 | 12 | 472.164 | 1 | 39.347 | 180.429 | 652.59 | 369.323 |
| 5-2 | 6 | 0.767 | 12 | 9.204 | 1 | 0.767 | 0.000 | 9.20 | 5.209 |
|  | 24 | 6.015 | 12 | 72.180 | 1 | 6.015 | 0.767 | 72.95 | 41.283 |
|  | 48 | 12.141 | 12 | 145.692 | 1 | 12.141 | 6.782 | 152.47 | 86.290 |
|  | 72 | 17.910 | 12 | 214.920 | 1 | 17.910 | 18.923 | 233.84 | 132.339 |
|  | 96 | 21.591 | 12 | 259.092 | 1 | 21.591 | 36.833 | 295.93 | 167.473 |
|  | 120 | 24.647 | 12 | 295.764 | 1 | 24.647 | 58.424 | 354.19 | 200.446 |
|  | 148 | 27.851 | 12 | 334.212 | 1 | 27.851 | 83.071 | 417.28 | 236.153 |
|  | 168 | 29.933 | 12 | 359.196 | 1 | 29.933 | 110.922 | 470.12 | 266.054 |

The average of the two permeation tests of Example 5 was calculated and is listed in Table 5C

TABLE 5C

| | µg/cm² | | | |
|---|---|---|---|---|
| Hours | Test 5-1 | Test 5-2 | Average of two tests | Std Dev |
| 6 | 12.414 | 5.209 | 8.812 | 5.095 |
| 24 | 77.014 | 41.283 | 59.149 | 25.266 |
| 48 | 158.110 | 86.290 | 122.200 | 50.784 |
| 72 | 229.436 | 132.339 | 180.888 | 68.658 |
| 96 | 282.195 | 167.473 | 224.834 | 81.121 |
| 120 | 323.513 | 200.446 | 261.980 | 87.022 |
| 148 | 346.078 | 236.153 | 291.116 | 77.729 |
| 168 | 369.323 | 266.054 | 317.689 | 73.022 |

Based on the permeation results of Example 5, listed in Table 5B, the following flux results listed in Table 5D below were obtained:

TABLE 5D

| | µg/cm²/hr | | | |
|---|---|---|---|---|
| Hours | Test 5-1 | Test 5-2 | Average of two tests | Std Dev |
| 6 | 2.069 | 0.868 | 1.469 | 0.846 |
| 24 | 3.209 | 1.720 | 2.465 | 1.053 |
| 48 | 3.294 | 1.798 | 2.546 | 1.058 |
| 72 | 3.187 | 1.838 | 2.512 | 0.954 |
| 96 | 2.940 | 1.745 | 2.342 | 0.845 |
| 120 | 2.696 | 1.670 | 2.183 | 0.725 |
| 148 | 2.338 | 1.596 | 1.967 | 0.525 |
| 168 | 2.198 | 1.584 | 1.891 | 0.435 |
| $F_{6-96}$ | 3.025 | 1.820 | 2.423 | 0.853 |
| CORR | 0.996 | 0.999 | 0.997 | 0.002 |

EXAMPLE 6

A Loratadine active matrix/adhesive matrix formulation was prepared having the formulation set forth in Table 6A below:

TABLE 6A

| Ingredient | Amount (gm) |
| --- | --- |
| Loratadine | 0.36 |
| Ethyl Acetate | 2.67 |
| BIO PSA 7-4302 (adhesive solution) containing 11.96 gm silicone adhesive (60% solids) | 19.93 |
| Total | 22.96 |

The formulation of Table 6A was prepared and incorporated into a permeation testing apparatus according to the same procedure as in Example 3.

The formulation of Example 6 was tested using a permeation cell with a definable surface area for permeation. The receptor of the permeation cell was Ethanol:water (40:60). Three permeation tests (6-1, 6-2, and 6-3) were conducted giving the results listed in Table 6B below:

TABLE 6B $\mu g/cm^2$

| Hours | Test 6-1 | Test 6-2 | Test 6-3 | Average of three tests | Std Dev |
| --- | --- | --- | --- | --- | --- |
| 6 | 103.382 | 105.542 | 89.338 | 99.421 | 8.798 |
| 24 | 385.736 | 387.593 | 348.952 | 374.094 | 21.793 |
| 48 | 637.848 | 659.757 | 591.666 | 629.757 | 34.759 |
| 72 | 832.501 | 854.233 | 769.620 | 818.785 | 43.942 |
| 96 | 897.573 | 954.671 | 857.260 | 903.168 | 48.946 |
| 124 | 972.628 | 1026.660 | 933.732 | 977.673 | 46.669 |
| 144 | 1041.228 | 1107.161 | 1003.008 | 1050.466 | 52.687 |
| 168 | 1051.728 | 1140.184 | 1036.631 | 1076.181 | 55.940 |

Based on the permeation results of Example 6, listed in Table 6B, the following flux results listed in Table 6C below were obtained:

TABLE 6C $\mu g/cm^2/hr$

| Hours | Test 6-1 | Test 6-2 | Test 6-3 | Average of three tests | Std Dev |
| --- | --- | --- | --- | --- | --- |
| 6 | 17.230 | 17.590 | 14.890 | 16.570 | 1.466 |
| 24 | 16.072 | 16.150 | 14.540 | 15.587 | 0.908 |
| 48 | 13.289 | 13.745 | 12.326 | 13.120 | 0.724 |
| 72 | 11.563 | 11.864 | 10.689 | 11.372 | 0.610 |
| 96 | 9.350 | 9.944 | 8.930 | 9.408 | 0.510 |
| 124 | 7.844 | 8.280 | 7.530 | 7.884 | 0.376 |
| 144 | 7.231 | 7.689 | 6.965 | 7.295 | 0.366 |
| 168 | 6.260 | 6.787 | 6.170 | 6.406 | 0.333 |
| $F_{6-96}$ | 8.831 | 9.407 | 8.499 | 8.912 | 0.459 |
| CORR | 0.970 | 0.977 | 0.976 | 0.974 | 0.004 |

EXAMPLE 7

A Loratadine active drug/adhesive matrix formulation was prepared having the formulation set forth in Table 7A below:

TABLE 7A

| Ingredient | Amount (gm) |
| --- | --- |
| Loratadine | 0.24 |
| Polyisobutylene (adhesive) MA-24 + mineral oil (adhesive solution) (25% solids) | 28.62 |
| Total | 28.86 |

The formulation of Table 7A was prepared and incorporated into a permeation testing apparatus according to the same procedure as in Example 3, using MA-24+ mineral oil as the adhesive solution and without the use of ethyl acetate.

The formulation of Example 7 was tested using a permeation cell with a definable surface area for permeation. The receptor of the permeation cell was Ethanol:water (40:60). Three permeation tests (7-1, 7-2, and 7-3) were conducted giving the results listed in Table 7B below:

TABLE 7B $\mu g/cm^2$

| Hours | Test 7-1 | Test 7-2 | Test 7-3 | Average of three tests | Std Dev |
| --- | --- | --- | --- | --- | --- |
| 6 | 16.075 | 2.405 | 15.945 | 11.475 | 7.855 |
| 24 | 99.938 | 67.530 | 113.135 | 93.534 | 23.467 |
| 48 | 214.922 | 184.259 | 249.768 | 216.316 | 32.777 |
| 72 | 310.962 | 294.490 | 354.921 | 320.124 | 32.240 |
| 96 | 334.402 | 323.299 | 388.632 | 348.778 | 34.958 |
| 124 | 350.720 | 342.504 | 415.032 | 369.419 | 39.715 |
| 144 | 360.886 | 352.968 | 420.276 | 378.043 | 36.788 |
| 168 | 359.021 | 358.228 | 421.273 | 379.507 | 36.172 |

Based on the permeation results of Example 7, listed in Table 7B, the following flux results listed in Table 7C below were obtained:

TABLE 7C $\mu g/cm^2/hr$

| Hours | Test 7-1 | Test 7-2 | Test 7-3 | Average of three tests | Std Dev |
| --- | --- | --- | --- | --- | --- |
| 6 | 2.679 | 0.401 | 2.658 | 1.913 | 1.309 |
| 24 | 4.164 | 2.814 | 4.714 | 3.897 | 0.978 |
| 48 | 4.478 | 3.839 | 5.204 | 4.507 | 0.683 |
| 72 | 4.319 | 4.090 | 4.929 | 4.446 | 0.434 |
| 96 | 3.483 | 3.368 | 4.048 | 3.633 | 0.364 |
| 124 | 2.828 | 2.762 | 3.347 | 2.979 | 0.320 |
| 144 | 2.506 | 2.451 | 2.919 | 2.625 | 0.255 |
| 168 | 2.137 | 2.132 | 2.508 | 2.259 | 0.215 |
| $F_{6-96}$ | 3.697 | 3.802 | 4.305 | 3.934 | 0.325 |
| CORR | 0.979 | 0.985 | 0.981 | 0.981 | 0.003 |

EXAMPLE 8

A active drug/adhesive matrix formulation was prepared having the formulation set forth in table 8A below:

TABLE 8A

| Ingredient | Amount (gm) |
| --- | --- |
| Loratadine | 0.12 |
| Ethyl Acetate | 0.89 |
| Silicone (adhesive) | 11.49 (60% solids) |
| BIO PSA 7-4302 (adhesive solution) | 19.14 |
| Total | 20.15 |

The formulation of Table 8A was prepared and incorporated into a permeation testing apparatus according to the same procedure as in Example 3.

The formulation of Example 8A was tested using a permeation cell with a definable surface area for permeation. The receptor of the permeation cell was Ethanol:water (40:60). Three permeation tests (8-1, 8-2, and 8-3) were conducted giving the results listed in Table 8B below:

TABLE 8B

| | μg/cm$^2$ | | | | |
|---|---|---|---|---|---|
| Hours | Test 8-1 | Test 8-2 | Test 8-3 | Average of three tests | Std Dev |
| 6 | 49.508 | 21.195 | 21.589 | 30.764 | 16.234 |
| 24 | 245.430 | 189.040 | 202.444 | 212.305 | 29.460 |
| 48 | 358.829 | 323.036 | 321.963 | 334.609 | 20.982 |
| 72 | 420.138 | 393.948 | 379.922 | 398.003 | 20.412 |
| 96 | 435.580 | 418.582 | 401.711 | 418.624 | 16.935 |
| 124 | 435.805 | 432.793 | 415.518 | 428.039 | 10.947 |
| 144 | 444.518 | 443.853 | 441.285 | 443.219 | 1.707 |
| 168 | 442.115 | 451.107 | 436.680 | 443.301 | 7.286 |

Based on the permeation results of Example 8, listed in Table 8B, the following flux results listed in Table 8C below were obtained:

TABLE 8C

| | μg/cm$^2$/hr | | | | |
|---|---|---|---|---|---|
| Hours | Test 8-1 | Test 8-2 | Test 8-3 | Average of three tests | Std Dev |
| 6 | 8.251 | 3.533 | 3.598 | 5.127 | 2.706 |
| 24 | 10.226 | 7.877 | 8.435 | 8.846 | 1.227 |
| 48 | 7.476 | 6.730 | 6.708 | 6.971 | 0.437 |
| 72 | 5.835 | 5.472 | 5.277 | 5.528 | 0.284 |
| 96 | 4.537 | 4.360 | 4.184 | 4.361 | 0.176 |
| 124 | 3.515 | 3.490 | 3.351 | 3.452 | 0.088 |
| 144 | 3.087 | 3.082 | 3.064 | 3.078 | 0.012 |
| 168 | 2.632 | 2.685 | 2.599 | 2.639 | 0.043 |
| $F_{6-96}$ | 4.069 | 4.317 | 4.037 | 4.141 | 0.154 |
| CORR | 0.920 | 0.945 | 0.930 | 0.932 | 0.013 |

EXAMPLE 9

A active drug/adhesive matrix formulation was prepared having the formulation set forth in Table 9A below:

TABLE 9A

| Ingredient | Amount (gm) |
|---|---|
| Loratadine | 0.24 |
| Ethyl Acetate | 1.78 |
| BIO PSA 7-4302 (adhesive solution) containing 11.63 silicone adhesive (60% solids) | 19.38 |
| Total | 21.4 |

The formulation of Table 9A was prepared and incorporated into a permeation testing apparatus according to the same procedure as in Example 3.

The formulation of Example 9A was tested using a permeation cell with a definable surface area for permeation. The receptor of the permeation cell was Ethanol:water (40:60). Three permeation tests (9-1, 9-2, and 9-3) were conducted giving the results listed in Table 9B below:

TABLE 9B

| | μg/cm$^2$ | | | | |
|---|---|---|---|---|---|
| Hours | Test 9-1 | Test 9-2 | Test 9-3 | Average of three tests | Std Dev |
| 6 | 70.513 | 52.306 | 34.329 | 52.383 | 18.092 |
| 24 | 325.937 | 331.333 | 293.360 | 316.877 | 20.544 |
| 48 | 639.013 | 547.878 | 503.103 | 563.331 | 69.260 |
| 72 | 809.531 | 697.645 | 650.643 | 719.273 | 81.622 |
| 96 | 856.208 | 750.846 | 704.606 | 770.553 | 77.699 |
| 124 | 892.737 | 784.874 | 746.189 | 807.933 | 75.947 |
| 144 | 928.925 | 836.425 | 766.745 | 844.032 | 81.357 |
| 168 | 919.161 | 849.990 | 812.193 | 860.448 | 54.245 |

Based on the permeation results of Example 9, listed in Table 9B, the following flux results listed in Table 9C below were obtained:

TABLE 9C

| | μg/cm$^2$/hr | | | | |
|---|---|---|---|---|---|
| Hours | Test 9-1 | Test 9-2 | Test 9-3 | Average of three tests | Std Dev |
| 6 | 11.752 | 8.718 | 5.722 | 8.730 | 3.015 |
| 24 | 13.581 | 13.806 | 12.223 | 13.203 | 0.856 |
| 48 | 13.313 | 11.414 | 10.481 | 11.736 | 1.443 |
| 72 | 11.243 | 9.690 | 9.037 | 9.990 | 1.134 |
| 96 | 8.919 | 7.821 | 7.340 | 8.027 | 0.809 |
| 124 | 7.199 | 6.330 | 6.018 | 6.516 | 0.612 |
| 144 | 6.451 | 5.809 | 5.325 | 5.861 | 0.565 |
| 168 | 5.471 | 5.059 | 4.834 | 5.122 | 0.323 |
| $F_{6-96}$ | 8.921 | 7.631 | 7.353 | 7.968 | 0.836 |
| CORR | 0.962 | 0.959 | 0.962 | 0.961 | 0.002 |

EXAMPLE 10

A active drug/adhesive matrix formulation was prepared having the formulation set forth in Table 10A below:

TABLE 10A

| Ingredient | Amount (gm) |
|---|---|
| Loratadine | 0.36 |
| Ethyl Acetate | 2.67 |
| BIO PSA 7-4302 (adhesive solution) containing 11.96 gm silicone adhesive (60% solids) | 19.93 |
| Total | 22.96 |

The formulation of Table 10A was prepared and incorporated into a permeation testing apparatus according to the same procedure as in Example 3.

The formulation of Example 10A was tested using a permeation cell with a definable surface area for permeation. The receptor of the permeation cell was Ethanol:water (40:60). Three permeation tests (10-1, 10-2, and 10-3) were conducted giving the results listed in Table 10B below:

TABLE 10B

| | μg/cm$^2$ | | | | |
|---|---|---|---|---|---|
| Hours | Test 10-1 | Test 10-2 | Test 10-3 | Average of three tests | Std Dev |
| 6 | 103.382 | 105.542 | 89.338 | 99.421 | 8.798 |
| 24 | 385.736 | 387.593 | 348.592 | 374.094 | 21.793 |

TABLE 10B-continued $\mu g/cm^2$

| Hours | Test 10-1 | Test 10-2 | Test 10-3 | Average of three tests | Std Dev |
|---|---|---|---|---|---|
| 48 | 637.848 | 659.757 | 591.666 | 629.757 | 34.759 |
| 72 | 832.501 | 854.233 | 769.620 | 818.785 | 43.942 |
| 96 | 897.573 | 954.671 | 857.260 | 903.168 | 48.946 |
| 124 | 972.628 | 1026.660 | 933.732 | 977.679 | 46.669 |
| 144 | 1041.228 | 1107.161 | 1003.008 | 1050.466 | 52.687 |
| 168 | 1051.728 | 1140.184 | 1036.631 | 1076.181 | 55.940 |

Based on the permeation results of Example 10, listed in Table 10B, the following flux results listed in Table 10C below were obtained:

TABLE 10C $\mu g/cm^2/hr$

| Hours | Test 10-1 | Test 10-2 | Test 10-3 | Average of three tests | Std Dev |
|---|---|---|---|---|---|
| 6 | 17.230 | 17.590 | 14.890 | 16.570 | 1.466 |
| 24 | 16.072 | 16.150 | 14.540 | 15.587 | 0.908 |
| 48 | 13.289 | 13.745 | 12.326 | 13.120 | 0.724 |
| 72 | 11.563 | 11.864 | 10.689 | 11.372 | 0.610 |
| 96 | 9.350 | 9.944 | 8.930 | 9.408 | 0.510 |
| 124 | 7.844 | 8.280 | 7.530 | 7.884 | 0.376 |
| 144 | 7.231 | 7.689 | 6.965 | 7.295 | 0.366 |
| 168 | 6.260 | 6.787 | 6.170 | 6.406 | 0.333 |
| $F_{6-96}$ | 8.831 | 9.407 | 8.499 | 8.912 | 0.459 |
| CORR | 0.970 | 0.977 | 0.976 | 0.974 | 0.004 |

EXAMPLE 11

A active drug/adhesive matrix formulation was prepared having the formulation set forth in Table 11A below:

TABLE 11A

| Ingredient | Amount (gm) |
|---|---|
| Loratadine | 0.4 |
| Ethyl Acetate | 3.0 |
| BIO PSA 7-4302 (adhesive solution) containing 17.6 gm silicone adhesive (60% solids) | 29.3 |
| Transcutol P (solvent) | 2.0 |
| Total | 34.7 |

The formulation of Table 11A was prepared and incorporated into a permeation testing apparatus according to the same procedure as in Example 3 using Transcutol P as an additional solvent.

The formulation of Example 11A was tested using a permeation cell with a definable surface area for permeation. The receptor of the permeation cell was Ethanol:water (40:60). Three permeation tests (11-1, 11-2, and 11-3) were conducted giving the results listed in Table 11B below:

TABLE 11B $\mu g/cm^2$

| Hours | Test 11-1 | Test 11-2 | Test 11-3 | Average of three tests | Std Dev |
|---|---|---|---|---|---|
| 6 | 133.990 | 155.952 | 140.876 | 143.606 | 11.233 |
| 24 | 515.838 | 553.145 | 539.020 | 536.001 | 18.836 |
| 30 | 555.286 | 591.475 | 589.167 | 578.643 | 20.260 |
| 48 | 683.414 | 725.466 | 718.901 | 709.260 | 22.623 |
| 54 | 695.520 | 751.848 | 742.940 | 730.103 | 30.279 |
| 72 | 783.265 | 845.732 | 833.738 | 820.912 | 33.150 |
| 78 | 782.751 | 837.382 | 845.070 | 821.734 | 33.979 |
| 99 | 868.499 | 913.301 | 877.658 | 886.486 | 23.670 |
| 120 | 918.598 | 970.121 | 944.529 | 944.416 | 25.762 |
| 144 | 946.115 | 1004.137 | 964.594 | 971.615 | 29.641 |
| 150 | 936.874 | 984.544 | 961.619 | 961.012 | 23.841 |
| 168 | 951.645 | 1006.483 | 993.268 | 983.799 | 28.619 |

Table 11C lists further data with respect to Test 11-3.

TABLE 11C

| Test # | Sampling Time (Hours) | Drug Conc. (µg/ml) | Receptor Volume (ml) | Drug Amount (µg) | Sampling Volume (ml) | Drug Loss due to Sampling (µg) | Cumulative Drug Loss (µg) | Cumulative Amount Permeated (µg) | Amount Permeated per cm² (µg/cm²) |
|---|---|---|---|---|---|---|---|---|---|
| 11-3 | 6 | 20.744 | 12 | 248.928 | 1 | 20.744 | 0.00 | 248.928 | 140.876 |
|  | 24 | 77.642 | 12 | 931.704 | 1 | 77.642 | 20.744 | 952.448 | 539.020 |
|  | 30 | 78.556 | 12 | 942.672 | 1 | 78.556 | 98.386 | 1041.058 | 589.167 |
|  | 48 | 91.113 | 12 | 1093.356 | 1 | 91.113 | 176.942 | 1270.298 | 718.901 |
|  | 54 | 87.060 | 12 | 1044.720 | 1 | 87.060 | 268.055 | 1312.775 | 742.940 |
|  | 72 | 93.175 | 12 | 1118.100 | 1 | 93.175 | 355.115 | 1473.215 | 833.738 |
|  | 78 | 87.079 | 12 | 1044.948 | 1 | 87.079 | 448.290 | 1493.238 | 845.070 |
|  | 99 | 84.621 | 12 | 1015.452 | 1 | 84.621 | 535.369 | 1550.821 | 877.658 |
|  | 120 | 87.416 | 12 | 1048.992 | 1 | 87.416 | 619.990 | 1668.982 | 944.529 |
|  | 144 | 83.086 | 12 | 997.032 | 1 | 83.086 | 707.406 | 1704.438 | 964.594 |
|  | 150 | 75.724 | 12 | 908.688 | 1 | 75.724 | 790.492 | 1699.180 | 961.619 |
|  | 168 | 74.074 | 12 | 888.888 | 1 | 74.074 | 866.216 | 1755.104 | 993.268 |

Based on the permeation results of Example 11, listed in Table 11B, the averages of the permeation tests were calculated and the flux results listed in Table 11D below were obtained:

TABLE 11D

| | | | μg/cm²/hr | | |
|---|---|---|---|---|---|
| Hours | Test 11-1 | Test 11-2 | Test 11-3 | Average of three tests | Std Dev |
| 6 | 22.332 | 25.992 | 23.479 | 23.934 | 1.872 |
| 24 | 21.493 | 23.048 | 22.459 | 22.333 | 0.785 |
| 30 | 18.510 | 19.716 | 19.639 | 19.288 | 0.675 |
| 48 | 14.238 | 15.114 | 14.977 | 14.776 | 0.471 |
| 54 | 12.880 | 13.923 | 13.758 | 13.520 | 0.561 |
| 72 | 10.879 | 11.746 | 11.580 | 11.402 | 0.460 |
| 78 | 10.035 | 10.736 | 10.834 | 10.535 | 0.436 |
| 99 | 8.773 | 9.225 | 8.865 | 8.954 | 0.239 |
| 120 | 7.655 | 8.084 | 7.871 | 7.870 | 0.215 |
| 144 | 6.570 | 6.973 | 6.699 | 6.747 | 0.206 |
| 150 | 6.246 | 6.564 | 6.411 | 6.407 | 0.159 |
| 168 | 5.665 | 5.991 | 5.912 | 5.856 | 0.170 |
| $F_{6-99}$ | 6.851 | 7.164 | 7.071 | 7.029 | 0.161 |
| CORR | 0.914 | 0.913 | 0.902 | 0.910 | |
| $F_{6-168}$ | 3.958 | 4.094 | 3.969 | 4.007 | 0.076 |
| CORR | 0.882 | 0.878 | 0.867 | 0.876 | |

EXAMPLE 12

A active drug/adhesive matrix formulation was prepared having the formulation set forth in Table 12A below:

TABLE 12A

| Ingredient | Amount (gm) |
|---|---|
| Loratadine | 0.4 |
| Ethyl Acetate | 3.0 |
| BIO PSA 7-4302 (adhesive solution) containing 17.6 gm silicone adhesive (60% solids) | 29.3 |
| Lauryl Acohol (solvent) | 2.0 |
| Total | 34.7 |

The formulation of Table 12A was prepared and incorporated into a permeation testing us according to the same procedure as in Example 3 using lauryl alcohol as an additional solvent.

The formulation of Example 12A was tested using a permeation cell with a definable surface area for permeation. The receptor of the permeation cell was Ethanol:water (40:60). Three permeation tests (12-1, 12-2, and 12-3) were conducted giving the results listed in Table 12B below:

TABLE 12B

| | | μg/cm² | | | |
|---|---|---|---|---|---|
| Hours | Test 12-1 | Test 12-2 | Test 12-3 | Average of three tests | Std Dev |
| 6 | 171.613 | 167.470 | 145.806 | 161.630 | 13.859 |
| 24 | 603.924 | 573.643 | 553.767 | 577.111 | 25.258 |
| 30 | 648.367 | 661.962 | 595.567 | 935.299 | 35.074 |
| 48 | 803.563 | 770.051 | 738.869 | 770.828 | 32.354 |
| 54 | 832.797 | 779.924 | 749.892 | 787.538 | 41.974 |
| 72 | 932.645 | 881.734 | 847.836 | 887.405 | 42.688 |
| 78 | 937.072 | 895.118 | 853.752 | 895.314 | 41.660 |
| 99 | 978.713 | 946.745 | 921.427 | 948.962 | 28.707 |
| 120 | 1019.499 | 994.321 | 969.105 | 994.308 | 25.197 |
| 144 | 1072.582 | 1013.288 | 1009.257 | 1031.709 | 35.454 |
| 150 | 1046.531 | 1027.470 | 989.674 | 1021.225 | 28.938 |
| 168 | 1064.410 | 1030.903 | 1035.502 | 1043.605 | 18.164 |

Table 12C lists further data with respect to Test 12-3.

TABLE 12C

| Test # | Sampling Time (Hours) | Drug Conc. (μg/ml) | Receptor Volume (ml) | Drug Amount (μg) | Sampling Volume (ml) | Drug Loss due to Sampling (μg) | Cumulative Drug Loss (μg) | Cumulative Amount Permeated (μg) | Amount Permeated per cm² (μg/cm²) |
|---|---|---|---|---|---|---|---|---|---|
| 12-3 | 6 | 21.470 | 12 | 257.640 | 1 | 21.470 | 0.000 | 257.640 | 145.806 |
| | 24 | 79.753 | 12 | 957.036 | 1 | 79.753 | 21.470 | 978.506 | 553.767 |
| | 30 | 79.262 | 12 | 951.144 | 1 | 79.262 | 101.223 | 1052.367 | 595.567 |
| | 48 | 93.758 | 12 | 1125.096 | 1 | 93.758 | 180.485 | 1305.581 | 738.869 |
| | 54 | 87.568 | 12 | 1050.816 | 1 | 87.568 | 274.243 | 1325.059 | 749.892 |
| | 72 | 94.693 | 12 | 1136.316 | 1 | 94.693 | 361.811 | 1498.127 | 847.836 |
| | 78 | 87.673 | 12 | 1052.076 | 1 | 87.673 | 456.504 | 1508.580 | 853.752 |
| | 99 | 90.332 | 12 | 1083.984 | 1 | 90.332 | 544.177 | 1628.161 | 921.427 |
| | 120 | 89.825 | 12 | 1077.900 | 1 | 89.825 | 634.509 | 1712.409 | 969.105 |
| | 144 | 88.252 | 12 | 1059.024 | 1 | 88.252 | 724.334 | 1783.358 | 1009.257 |
| | 150 | 78.014 | 12 | 936.168 | 1 | 78.014 | 812.586 | 1748.754 | 989.674 |
| | 168 | 78.261 | 12 | 939.132 | 1 | 78.261 | 890.600 | 1829.732 | 1035.502 |

Based on the permeation results of Example 12, listed in Table 12B, the averages of the permeation tests were calculated and the flux results listed in Table 12D below were obtained:

TABLE 12D

| | | μg/cm²/hr | | | |
|---|---|---|---|---|---|
| Hours | Test 12-1 | Test 12-2 | Test 12-3 | Average of three tests | Std Dev |
| 6 | 28.602 | 27.912 | 24.301 | 26.938 | 2.310 |
| 24 | 25.164 | 23.902 | 23.074 | 24.046 | 1.052 |
| 30 | 21.612 | 22.065 | 19.852 | 21.177 | 1.169 |
| 48 | 16.741 | 16.043 | 15.393 | 16.059 | 0.674 |
| 54 | 15.422 | 14.443 | 13.887 | 14.584 | 0.777 |
| 72 | 12.953 | 12.246 | 11.776 | 12.325 | 0.593 |
| 78 | 12.014 | 11.476 | 10.946 | 11.478 | 0.534 |
| 99 | 9.886 | 9.563 | 9.307 | 9.585 | 0.290 |
| 120 | 8.496 | 8.286 | 8.076 | 8.286 | 0.210 |
| 144 | 7.448 | 7.037 | 7.009 | 7.165 | 0.246 |
| 150 | 6.977 | 6.850 | 6.598 | 6.808 | 0.193 |
| 168 | 6.336 | 6.136 | 6.164 | 6.212 | 0.108 |
| $F_{6-99}$ | 7.791 | 7.344 | 7.339 | 7.492 | 0.260 |

TABLE 12D-continued

| | | | $\mu g/cm^2/hr$ | | |
|---|---|---|---|---|---|
| Hours | Test 12-1 | Test 12-2 | Test 12-3 | Average of three tests | Std Dev |
| CORR | 0.905 | 0.902 | 0.912 | 0.906 | |
| $F_{6-168}$ | 4.176 | 4.036 | 4.197 | 4.136 | 0.088 |
| CORR | 0.852 | 0.859 | 0.879 | 0.863 | |

EXAMPLE 13

A Loratadine reservoir and active drug/adhesive matrix formulation was prepared having the formulation set forth in Table 13A below:

TABLE 13A

| Ingredient | Amount (gm) |
|---|---|
| Donor Solution | |
| Loratadine | 0.35 |
| Ethanol | 22.0 (95%) |
| Water | 27.0 |
| Total | 49.35 |
| Membrane | Polyethylene |
| Active Drug/Adhesive Matrix | |
| Loratadine | 0.12 gm |
| BIO PSA 7-4302 (adhesive solution) containing 11.49 gm silicone adhesive (60% solids) | 19.14 gm |
| Ethyl acetate solvent | 0.89 gm |
| Total | 20.15 gm |

The formulation of Table 13A was prepared and incorporated into a permeation testing apparatus according to the following procedure:

1. Loratadine is dissolved with ethanol and water and the solution is placed into the donor cell.
2. Loratadine is dispersed in the adhesive solution and ethyl acetate solvent to form the active drug/adhesive matrix.
3. The polyethylene membrane is coated with active drug/adhesive matrix and placed against the donor cell and dried. The coated surface of the membrane is positioned opposite from the donor cell.
4. Thereafter, the human cadaver skin is placed between the coated membrane surface and the receptor cell and the apparatus is secured.

The formulation of Example 13 was tested using a permeation cell with a definable surface area for permeation. The receptor of the permeation cell was Ethanol:water (40:60). Three permeation tests (13-1, 13-2, and 13-3) were conducted giving the results listed in Table 13B below:

TABLE 13B

| | | | $\mu g/cm^2$ | | |
|---|---|---|---|---|---|
| Hours | Test 13-1 | Test 13-2 | Test 13-3 | Average of three tests | Std Dev |
| 6 | 72.594 | 58.406 | 69.079 | 66.694 | 7.387 |
| 24 | 217.680 | 175.542 | 197.278 | 196.833 | 21.073 |
| 30 | 255.681 | 203.923 | 227.740 | 229.115 | 25.906 |
| 48 | 348.695 | 283.263 | 310.261 | 314.073 | 32.882 |
| 54 | 385.778 | 308.526 | 336.586 | 343.630 | 39.105 |
| 72 | 487.268 | 391.914 | 419.969 | 433.050 | 49.004 |
| 78 | 523.816 | 419.585 | 446.677 | 463.359 | 54.081 |
| 96 | 629.393 | 505.149 | 532.631 | 555.721 | 65.262 |
| 102 | 662.817 | 528.167 | 555.429 | 582.138 | 71.188 |
| 120 | 762.760 | 613.895 | 634.252 | 671.302 | 80.061 |
| 144 | 920.453 | 741.930 | 759.623 | 807.335 | 98.361 |
| 168 | 1068.287 | 865.187 | 872.726 | 935.400 | 115.145 |

Table 13C lists further data with respect to Test 13-3.

TABLE 13C

| Test # | Sampling Time (Hours) | Drug Conc. (µg/ml) | Receptor Volume (ml) | Drug amount (µg) | Sampling Volume (ml) | Drug Loss due to Sampling (µg) | Cumulative Drug Loss (µg) | Cumulative Amount Permeated (µg) | Amount Permeated per $cm^2$ (µg/$cm^2$) |
|---|---|---|---|---|---|---|---|---|---|
| 13-3 | 6 | 10.987 | 4 | 43.948 | 4 | 43.948 | 0.000 | 43.948 | 69.079 |
| | 24 | 20.390 | 4 | 81.560 | 4 | 81.560 | 43.948 | 125.508 | 197.278 |
| | 30 | 4.845 | 4 | 19.380 | 4 | 19.380 | 125.508 | 144.888 | 227.740 |
| | 48 | 13.125 | 4 | 42.500 | 4 | 52.500 | 144.888 | 197.388 | 310.261 |
| | 54 | 4.187 | 4 | 16.748 | 4 | 16.748 | 197.388 | 214.136 | 336.586 |
| | 72 | 13.262 | 4 | 53.048 | 4 | 53.048 | 214.136 | 267.184 | 419.969 |
| | 78 | 4.248 | 4 | 16.992 | 4 | 16.992 | 267.184 | 284.176 | 446.677 |
| | 96 | 13.671 | 4 | 54.684 | 4 | 54.684 | 284.176 | 338.860 | 532.631 |
| | 102 | 3.626 | 4 | 14.504 | 4 | 14.504 | 338.860 | 353.364 | 555.429 |
| | 120 | 13.014 | 4 | 52.056 | 4 | 52.056 | 353.364 | 405.420 | 637.252 |
| | 144 | 19.463 | 4 | 77.852 | 4 | 77.852 | 405.420 | 483.272 | 759.623 |
| | 168 | 17.989 | 4 | 71.956 | 4 | 71.956 | 483.272 | 555.228 | 872.726 |

Based on the permeation results of Example 13, listed in Table 13B, the averages of the permeation test were calculated and the flux results listed in Table 13D below were obtained:

TABLE 13D

| | | | μ/cm²/hr | | |
|---|---|---|---|---|---|
| Hours | Test 13-1 | Test 13-2 | Test 13-3 | Average of three tests | Std Dev |
| 6 | 12.099 | 9.735 | 11.513 | 11.116 | 1.231 |
| 24 | 9.070 | 7.314 | 8.220 | 8.201 | 0.878 |
| 30 | 8.523 | 6.797 | 7.591 | 7.637 | 0.864 |
| 48 | 7.264 | 5.901 | 6.464 | 6.543 | 0.685 |
| 54 | 7.144 | 5.713 | 6.233 | 6.364 | 0.724 |
| 72 | 6.768 | 5.443 | 5.833 | 6.015 | 0.681 |
| 78 | 6.716 | 5.379 | 5.727 | 5.941 | 0.693 |
| 96 | 6.556 | 5.262 | 5.548 | 5.789 | 0.680 |
| 102 | 6.498 | 5.178 | 5.445 | 5.707 | 0.698 |
| 120 | 6.356 | 5.116 | 5.310 | 5.594 | 0.667 |
| 144 | 6.392 | 5.152 | 5.275 | 5.606 | 0.683 |
| 168 | 6.359 | 5.150 | 5.195 | 5.568 | 0.685 |

EXAMPLE 14

A Loratadine reservoir and active drug/adhesive matrix formulation was prepared having the formulation set forth in Table 14A below:

TABLE 14A

| Ingredient | Amount (gm) |
|---|---|
| Donor Solution | |
| Loratadine | 0.35 |
| Ethanol | 22.0 (95%) |
| Water | 27.0 |
| Total | 49.35 |
| Membrane | Polyethylene |

TABLE 14A-continued

| Ingredient | Amount (gm) |
|---|---|
| Active Drug/Adhesive Matrix | |
| Loratadine | 0.24 gm |
| BIO PSA 7-4302 (adhesive solution) containing 11.63 gm silicone adhesive (60% solids) | 19.38 gm |
| Ethyl acetate solvent | 1.78 gm |
| Total | 21.4 gm* |

*Reflects removal of solvent from formulation upon drying

The formulation of Example 14 was prepared and incorporated into a permeation testing apparatus according to the procedure as in Example 13.

The formulation of Example 14 was tested using a permeation cell with a definable surface area for permeation. The receptor of the permeation cell was Ethanol:water (40:60). Three permeation tests (14-1, 14-2, and 14-3) were conducted giving the results listed in Table 14B below:

TABLE 14B

| | | | μg/cm² | | |
|---|---|---|---|---|---|
| Hours | Test 14-1 | Test 14-2 | Test 14-3 | Average of three tests | Std Dev |
| 6 | 99.616 | 93.914 | 65.244 | 86.258 | 18.421 |
| 24 | 289.299 | 264.313 | 215.108 | 256.240 | 37.749 |
| 30 | 329.217 | 303.791 | 247.476 | 293.495 | 41.832 |
| 48 | 407.865 | 397.793 | 316.888 | 374.182 | 49.873 |
| 54 | 434.033 | 430.324 | 339.025 | 401.127 | 53.814 |
| 72 | 510.588 | 523.829 | 405.564 | 479.994 | 64.797 |
| 78 | 536.221 | 556.542 | 427.281 | 506.681 | 69.509 |
| 96 | 617.391 | 654.782 | 494.782 | 588.985 | 83.697 |
| 102 | 638.743 | 684.929 | 511.311 | 611.661 | 89.922 |
| 120 | 713.411 | 777.743 | 574.052 | 688.402 | 104.123 |
| 144 | 828.802 | 914.128 | 671.500 | 804.810 | 123.080 |
| 168 | 935.549 | 1041.830 | 761.138 | 912.839 | 141.717 |

Table 14C lists further data with respect to Test 14-3.

TABLE 14C

| Test # | Sampling Time (Hours) | Drug Conc. (μg/ml) | Receptor Volume (ml) | Drug amount (μg) | Sampling Volume (ml) | Drug Loss due to Sampling (μg) | Cumulative Drug Loss (μg) | Cumulative Amount Permeated (μg) | Amount Permeated per cm² (μg/cm²) |
|---|---|---|---|---|---|---|---|---|---|
| 14-3 | 6 | 10.377 | 1 | 41.508 | 4 | 41.508 | 0.000 | 41.508 | 65.244 |
| | 24 | 23.836 | 4 | 95.344 | 4 | 95.344 | 41.508 | 136.852 | 215.108 |
| | 30 | 5.148 | 4 | 20.592 | 4 | 20.592 | 136.852 | 157.444 | 247.476 |
| | 48 | 11.040 | 4 | 44.160 | 4 | 44.160 | 157.444 | 201.604 | 316.888 |
| | 54 | 3.521 | 4 | 14.084 | 4 | 14.084 | 201.604 | 215.688 | 339.025 |
| | 72 | 10.583 | 4 | 42.332 | 4 | 42.332 | 215.688 | 258.020 | 405.564 |
| | 78 | 3.454 | 4 | 13.816 | 4 | 13.816 | 258.020 | 271.836 | 427.281 |
| | 96 | 10.736 | 4 | 42.944 | 4 | 42.944 | 271.836 | 314.780 | 494.782 |
| | 102 | 2.629 | 4 | 10.516 | 4 | 10.516 | 314.780 | 325.296 | 511.311 |
| | 120 | 9.979 | 4 | 39.916 | 4 | 39.916 | 325.296 | 365.212 | 574.052 |
| | 144 | 15.499 | 4 | 61.996 | 4 | 61.996 | 365.212 | 427.208 | 671.500 |
| | 168 | 14.257 | 4 | 57.028 | 4 | 57.028 | 427.208 | 484.236 | 761.138 |

Based on the permeation results of Example 14, listed in Table 14B, the averages of the permeation tests were calculated and the flux results listed in Table 14D below were obtained:

TABLE 14D $\mu g/cm^2/hr$

| Hours | Test 14-1 | Test 14-2 | Test 14-3 | Average of three tests | Std Dev |
|---|---|---|---|---|---|
| 6 | 16.603 | 15.652 | 10.874 | 14.376 | 3.070 |
| 24 | 12.054 | 11.013 | 8.963 | 10.677 | 1.573 |
| 30 | 10.974 | 10.126 | 8.249 | 9.783 | 1.394 |
| 48 | 8.497 | 8.287 | 6.602 | 7.795 | 1.039 |
| 54 | 8.038 | 7.969 | 6.278 | 7.428 | 0.997 |
| 72 | 7.092 | 7.275 | 5.633 | 6.667 | 0.900 |
| 78 | 6.875 | 7.135 | 5.478 | 6.496 | 0.891 |
| 96 | 6.431 | 6.821 | 5.154 | 6.135 | 0.872 |
| 102 | 6.262 | 6.715 | 5.013 | 5.997 | 0.882 |
| 120 | 5.945 | 6.481 | 4.784 | 5.737 | 0.868 |
| 144 | 5.756 | 6.348 | 4.663 | 5.589 | 0.855 |
| 168 | 5.569 | 6.201 | 4.531 | 5.434 | 0.844 |
| $F_{6-96}$ | 5.283 | 5.906 | 4.439 | 5.209 | 0.736 |
| CORR | 0.979 | 0.992 | 0.983 | | |

EXAMPLE 15

A Loratadine reservoir and active drug/adhesive matrix formulation was prepared having the formulation set forth in Table 15A below:

TABLE 15A

| Ingredient | Amount (gm) |
|---|---|
| Donor Solution | |
| Loratadine | 0.17 |
| Ethanol | 10.93 (95%) |
| Water | 13.4 |
| Klucel HF (gelling agent/enhancer) | 0.50 |
| Total | 25.0 gm |
| Membrane | Polyethylene |
| Active Drug/Adhesive Matrix | |
| Loratadine | 0.12 gm |
| BIO PSA 7-4302 (adhesive solution) containing 11.49 gm silicone adhesive (60% solids) | 19.14 gm |
| Ethyl acetate solvent | 0.89 gm |
| Total | 20.15 gm |

The formulation of Table 15A was prepared and incorporated into a permeation testing apparatus according to the following procedure:
1. Loratadine is dissolved with ethanol and water, Klucel HF is added and the solution is placed into the donor cell.
2. Loratadine is dispersed in the adhesive solution and ethyl acetate solvent to form the active drug/adhesive matrix.
3. The polyethylene membrane is coated with active drug/adhesive matrix and placed against the donor cell and dried. The coated surface of the membrane is positioned opposite from the donor cell.
4. Thereafter, the human cadaver skin is placed between the coated membrane surface and the receptor cell and the apparatus is secured.

The formulation of Example 15 was tested using a permeation cell with a definable surface area for permeation. The receptor of the permeation cell was Ethanol:water (40:60). Three permeation tests (15-1, 15-2, and 15-3) were conducted giving the results listed in Table 15B below:

TABLE 15B $\mu g/cm^2$

| Hours | Test 15-1 | Test 15-2 | Test 15-3 | Average of three tests | Std Dev |
|---|---|---|---|---|---|
| 6 | 30.400 | 31.356 | 33.475 | 31.744 | 1.574 |
| 24 | 113.504 | 96.723 | 104.500 | 104.909 | 8.398 |
| 30 | 138.050 | 114.351 | 120.220 | 124.207 | 12.342 |
| 48 | 220.527 | 176.029 | 183.955 | 193.504 | 23.736 |
| 54 | 245.590 | 194.380 | 203.129 | 214.366 | 27.392 |
| 72 | 336.788 | 265.985 | 281.761 | 294.845 | 37.171 |
| 78 | 359.116 | 286.556 | 303.001 | 316.224 | 38.044 |
| 96 | 450.921 | 350.096 | 383.057 | 394.691 | 51.410 |
| 120 | 591.832 | 455.829 | 507.498 | 518.386 | 68.652 |
| 144 | 685.488 | 556.102 | 631.384 | 624.325 | 64.981 |
| 168 | 780.272 | 635.766 | 730.428 | 715.489 | 73.402 |

Table 15C lists further data with respect to Test 15-3.

TABLE 15C

| Test # | Sampling Time (Hours) | Drug Conc. (μg/ml) | Receptor Volume (ml) | Drug Amount (μg) | Sampling Volume (ml) | Drug Loss due to Sampling (μg) | Cumulative Drug Loss (μg) | Cumulative Amount Permeated (μg) | Amount Permeated per cm² (μg/cm²) |
|---|---|---|---|---|---|---|---|---|---|
| 15-3 | 6 | 4.550 | 13 | 59.150 | 1 | 4.550 | 0.000 | 59.150 | 33.475 |
| | 24 | 13.854 | 13 | 180.102 | 1 | 13.854 | 4.550 | 184.652 | 104.500 |
| | 30 | 14.925 | 13 | 194.025 | 1 | 14.925 | 18.404 | 212.429 | 120.220 |
| | 48 | 22.440 | 13 | 291.720 | 1 | 22.440 | 33.329 | 325.049 | 183.955 |
| | 54 | 23.320 | 13 | 303.160 | 1 | 23.320 | 55.769 | 358.929 | 203.129 |
| | 72 | 32.214 | 13 | 418.782 | 1 | 32.214 | 79.089 | 497.871 | 281.761 |
| | 78 | 32.623 | 13 | 424.099 | 1 | 32.623 | 111.303 | 535.402 | 303.001 |
| | 96 | 40.995 | 13 | 532.935 | 1 | 40.995 | 143.926 | 676.861 | 383.057 |
| | 120 | 54.756 | 13 | 711.828 | 1 | 54.756 | 184.921 | 896.749 | 507.498 |
| | 144 | 67.383 | 13 | 875.979 | 1 | 67.383 | 239.677 | 1115.656 | 631.384 |
| | 168 | 75.622 | 13 | 983.606 | 1 | 75.662 | 307.060 | 1290.666 | 730.428 |

Based on the permeation results of Example 15, listed in Table 15B, the averages of the permeation tests were calculated and the flux results listed in Table 15D below were obtained:

TABLE 15D

| | μg/cm$^2$/hr | | | | |
|---|---|---|---|---|---|
| Hours | Test 15-1 | Test 15-2 | Test 15-3 | Average of three tests | Std Dev |
| 6 | 5.067 | 5.226 | 5.579 | 5.291 | 0.262 |
| 24 | 4.729 | 4.030 | 4.354 | 4.371 | 0.350 |
| 30 | 4.602 | 3.812 | 4.007 | 4.140 | 0.411 |
| 48 | 4.594 | 3.667 | 3.832 | 4.031 | 0.495 |
| 54 | 4.548 | 3.600 | 3.762 | 3.970 | 0.507 |
| 72 | 4.678 | 3.694 | 3.913 | 4.095 | 0.516 |
| 78 | 4.604 | 3.674 | 3.885 | 4.054 | 0.488 |
| 96 | 4.697 | 3.647 | 3.990 | 4.111 | 0.536 |
| 120 | 4.932 | 3.799 | 4.229 | 4.320 | 0.572 |
| 144 | 4.760 | 3.862 | 4.385 | 4.336 | 0.451 |
| 168 | 4.644 | 3.784 | 4.348 | 4.259 | 0.437 |
| $F_{6-96}$ | 4.651 | 3.544 | 3.830 | 4.008 | 0.575 |
| CORR | 1.000 | 1.000 | 0.998 | | |

EXAMPLE 16

A Loratadine reservoir and active drug/adhesive matrix formulation was prepared having the formulation of Table 16A below:

TABLE 16A

| Ingredient | Amount (gm) |
|---|---|
| Donor Solution | |
| Loratadine | 0.17 |
| Ethanol | 10.93 (95%) |
| Water | 13.4 |
| Klucel HF (gelling agent/enhancer) | 0.50 |
| Total | 25.0 gm |
| Membrane | Polyethylene |

TABLE 16A-continued

| Ingredient | Amount (gm) |
|---|---|
| Active Drug/Adhesive Matrix | |
| Loratadine | 0.24 gm |
| BIO PSA 7-4302 (adhesive solution) containing 11.63 gm silicone adhesive (60% solids) | 19.38 gm |
| Ethyl acetate solvent | 1.78 gm |
| Total | 21.4 gm |

The formulation of Example 16 was prepared and incorporated into a permeation testing apparatus according to the procedure as in Example 15.

The formulation of Example 16 was tested using a permeation cell with a definable surface area for permeation. The receptor of the permeation cell was Ethanol:water (40:60). Three permeation tests (16-1, 16-2, and 16-3) were conducted giving the results listed in Table 16B below:

TABLE 16B

| | μg/cm$^2$ | | | | |
|---|---|---|---|---|---|
| Hours | Test 16-1 | Test 16-2 | Test 16-3 | Average of three tests | Std Dev |
| 6 | 36.962 | 56.230 | 36.616 | 43.269 | 11.226 |
| 24 | 123.022 | 152.233 | 110.046 | 128.434 | 21.608 |
| 30 | 144.736 | 172.600 | 126.108 | 147.815 | 23.398 |
| 48 | 219.344 | 253.782 | 185.170 | 219.432 | 34.306 |
| 54 | 248.951 | 275.052 | 203.915 | 242.639 | 35.986 |
| 72 | 341.293 | 369.066 | 266.361 | 325.573 | 53.126 |
| 78 | 367.063 | 390.341 | 275.970 | 344.458 | 60.444 |
| 96 | 469.268 | 481.973 | 342.796 | 431.346 | 76.949 |
| 120 | 624.439 | 618.731 | 449.999 | 564.390 | 99.106 |
| 144 | 748.033 | 737.652 | 533.364 | 673.016 | 121.054 |
| 168 | 854.492 | 842.808 | 607.081 | 768.127 | 139.592 |

Table 16C lists further data with respect to Test 16-3.

TABLE 16C

| Test # | Sampling Time (Hours) | Drug Conc. (μg/ml) | Receptor Volume (ml) | Drug Amount (μg) | Sampling Volume (ml) | Drug Loss due to Sampling (μg) | Cumulative Drug Loss (μg) | Cumulative Amount Permeated (μg) | Amount Permeated per cm$^2$ (μg/cm$^2$) |
|---|---|---|---|---|---|---|---|---|---|
| 16-3 | 6 | 4.977 | 13 | 64.701 | 1 | 4.977 | 0.000 | 64.701 | 36.616 |
| | 24 | 14.575 | 13 | 189.475 | 1 | 14.575 | 4.977 | 194.452 | 110.046 |
| | 30 | 15.637 | 13 | 203.281 | 1 | 15.637 | 19.552 | 222.833 | 126.108 |
| | 48 | 22.462 | 13 | 292.006 | 1 | 22.462 | 35.189 | 327.195 | 185.170 |
| | 54 | 23.282 | 13 | 302.666 | 1 | 23.282 | 57.651 | 360.317 | 203.915 |
| | 72 | 29.979 | 13 | 389.727 | 1 | 29.979 | 80.933 | 470.660 | 266.361 |
| | 78 | 28.979 | 13 | 376.727 | 1 | 28.979 | 110.912 | 487.639 | 275.970 |
| | 96 | 35.833 | 13 | 465.829 | 1 | 35.833 | 139.891 | 605.720 | 342.796 |
| | 120 | 47.648 | 13 | 619.424 | 1 | 47.648 | 175.724 | 795.148 | 449.999 |
| | 144 | 55.314 | 13 | 719.082 | 1 | 55.314 | 223.372 | 942.454 | 533.364 |
| | 168 | 61.079 | 13 | 794.027 | 1 | 61.079 | 278.686 | 1072.713 | 607.081 |

Based on the permeation results of Example 16, listed in Table 16B, the averages of the permeation tests were calculated and the flux results listed in Table 16D below were obtained:

TABLE 16D

| | | μg/cm²/hr | | | |
|---|---|---|---|---|---|
| Hours | Test 16-1 | Test 16-2 | Test 16-3 | Average of three tests | Std Dev |
| 6 | 6.160 | 9.372 | 6.103 | 7.212 | 1.871 |
| 24 | 5.126 | 6.343 | 4.585 | 5.351 | 0.900 |
| 30 | 4.825 | 5.753 | 4.204 | 4.927 | 0.780 |
| 48 | 4.570 | 5.287 | 3.858 | 4.572 | 0.715 |
| 54 | 4.610 | 5.094 | 3.776 | 4.493 | 0.666 |
| 72 | 4.740 | 5.126 | 3.699 | 4.522 | 0.738 |
| 78 | 4.706 | 5.004 | 3.583 | 4.416 | 0.775 |
| 96 | 4.888 | 5.021 | 3.571 | 4.493 | 0.802 |
| 120 | 5.204 | 5.156 | 3.750 | 4.703 | 0.826 |
| 144 | 5.195 | 5.123 | 3.704 | 4.674 | 0.841 |
| 168 | 5.086 | 5.017 | 3.614 | 4.572 | 0.831 |
| $F_{6-96}$ | 4.722 | 4.647 | 3.318 | 4.229 | 0.790 |
| CORR | 0.998 | 0.999 | 0.999 | | |

In vitro skin permeation studies with cadaver skin quantitatively predict the pharmacokinetics and extent of drug absorption from the transdermal delivery dosage form. Matching in vitro skin donors to the in vivo population improves the correlation. Further improvements in this correlation are achieved by matching application sites.

it will be readily apparent that various modifications to the invention may be made by those killed in the art without departing from the scope of this invention. For example, many different transdermal delivery systems may be utilized in order to obtain the relative release rates and plasma levels described herein. Further, it is possible that mean values for plasma concentrations over a particular patient population for a particular described time point along the dosing interval may vary from the plasma concentration ranges described herein for that time point. Such obvious modifications are considered to be within the scope of the appended claims.

What is claimed:

1. A method of effectively treating seasonal allergic rhinitus, chronic idiopathic urticaria, or both conditions in a human patient, comprising administering loratadine transdermally to the human patient by applying a transdermal delivery system comprising (i) an active agent consisting of loratadine or a pharmaceutically acceptable salt thereof, (ii) a polymer, (iii) a softening agent; and (iv) a solvent, to the skin of a patient, and maintaining said transdermal delivery system in contact with the skin of the patient for at least 5 days, said transdermal delivery system maintaining an effective mean relative release rate to provide a therapeutic blood level of said loratadine within three days from the initiation of the dosing interval, and thereafter maintaining a therapeutic blood level until the end of at least the five-day dosing interval, said transdermal delivery device maintaining a plasma level of loratadine at steady state of about 3 ng/ml;

said transdermal delivery system having a mean relative release rate of from about 2.8 μg/cm²/hr to about 16.2 μg/cm²/hr of the transdermal delivery system surface area at 24 hours;

from about 2.3 μg/cm²/hr to about 13.7 μg/cm²/hr of the transdermal delivery system surface area at 48 hours;

from about 2.0 μg/cm²/hr to about 11.9 μg/cm²/hr of the transdermal delivery system surface area at 72 hours;

and a mean relative release rate of from about 1.8 μg/cm²/hr to about 9.9 μg/cm²/hr of the transdermal delivery system surface area at 96 hours; as determined via an in-vitro permeation test utilizing a Valia-Chien cell where the membrane is a human cadaver skin, said cell having a receptor chamber containing a 40:60 mixture of ethanol:water.

2. The method of claim 1 wherein the plasma level of loratadine at 48 hours does not decrease by more than 30% over the next 72 hours.

3. The method of claim 1, further comprising maintaining an effective mean relative release rate of said transdermal delivery system to provide a substantially first order plasma level increase of loratadine from the initiation of the dosing interval until about 48 to about 72 hours after the initiation of the dosing interval; and thereafter providing an effective mean relative release rate to provide a substantially zero order plasma level fluctuation of loratadine until the end of at least the five-day dosing interval.

4. The method of claim 1, further comprising providing a mean relative release rate of loratadine from said transdermal delivery system to provide a plasma level of loratadine of at least about 0.1 ng/ml within about 6 hours after application of said transdermal delivery system onto the skin of the patient.

5. The method of claim 1, wherein said therapeutic plasma level is maintained from about 0.1 ng/ml to about 3.3 ng/ml during the dosing interval for said transdermal delivery system.

6. The method of claim 1, wherein said transdermal delivery system has a mean relative release rate from about 1.0 μg/hour/cm² to about 30.0 μg/hour/cm².

7. The method of claim 1, wherein said transdermal delivery system provides an in-vitro cumulative amount of permeation of from about 63 μg/cm² to about 388 μg/cm² of the transdermal delivery system surface area at 24 hours; from about 105 μg/cm² to about 660 μg/cm² of the transdermal delivery system surface area at 48 hours; and from about 139 μg/cm² to about 854 μg/cm² of the transdermal delivery system surface area at 72 hours; and from about 162 μg/cm² to about 955 μg/cm² of the transdermal delivery system surface area at 96 hours; as determined via an in-vitro permeation test utilizing a Valia-Chien cell where the membrane is a human cadaver skin and said cell has a receptor chamber containing a 40:60 mixture of ethanol:water.

8. A transdermal delivery system comprising (i) an active agent consisting of loratadine or a pharmaceutically acceptable salt thereof, (ii) a polymer, (iii) a softening agent; and (iv) a solvent, the transdermal delivery system provides a mean relative release rate of from about 2.8 μg/cm²/hr to about 16.2 μg/cm²/hr of the transdermal delivery system surface area at 24 hours;

from about 2.3 μg/cm²/hr to about 13.7 μg/cm²/hr of the transdermal delivery system surface area at 48 hours;

from about 2.0 μg/cm²/hr to about 11.9 μg/cm²/hr of the transdermal delivery system surface area at 72 hours; and from about 1.8 μg/cm²/hr to about 9.9 μg/cm²/hr of the transdermal delivery system surface area at 96 hours; as determined via an in-vitro permeation test utilizing a Valia-Chien cell where the membrane is a human cadaver skin and said cell having a receptor chamber containing a 40:60 mixture of ethanol:water; said transdermal delivery system maintaining an effective mean relative release rate to provide a therapeutic blood level of said loratadine within 36 hours from the initiation of the dosing interval, and a plasma level of loratadine of at least about 0.1 ng/ml by about 6 hours after application of said transdermal delivery system onto the skin of a human patient; said transdermal delivery system maintaining a therapeutic blood level until the end of at least a five-day dosing interval and a plasma level of loratadine at steady state of about 3 ng/ml.

9. The transdermal delivery system of claim 8, which provides an in-vitro cumulative amount of permeation of from about 63 μg/cm² to about 388 μg/cm² of the transdermal delivery system surface area at 24 hours; from about 105 μg/cm² to about 660 μg/cm² of the transdermal delivery system surface area at 48 hours; and from about 139 μg/cm² to about 854 μg/cm² of the transdermal delivery system surface area at 72 hours, as determined via an in-vitro permeation test utilizing a Valia-Chien cell where the membrane is a human cadaver skin and said cell has a receptor chamber containing a 40:60 mixture of ethanol:water.

10. The transdermal delivery system of claim 8, comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of loratadine base or of a pharmaceutically acceptable salt thereof and 0.1 to 30% of a solvent for the loratadine or salt thereof.

11. The transdermal delivery system of claim 8, which is a laminated composite comprising (a) a polymer backing layer that is substantially impermeable to loratadine or the pharmaceutically acceptable salt thereat and (b) a reservoir layer comprising an acrylate or silicone based pressure-sensitive adhesive, 0.1 to 20% of loratadine base or of a pharmaceutically acceptable salt thereof, 0.1 to 30% of an ester of a carboxylic acid acting as a softening agent and 0.1 to 30% of a solvent for loratadine having at least one acidic group.

12. The transdermal delivery system of claim 8, wherein said therapeutic plasma level is maintained from about 0.1 ng/ml to about 3.3 ng/ml during the dosing interval for said transdermal delivery system.

13. The transdermal delivery system of claim 8, wherein said transdermal delivery system has a mean relative release rate from about 1.0 μg/hour/cm² to about 30.0 μg/hour/cm² of the transdermal delivery system surface area.

14. The transdermal delivery system of claim 8, wherein said transdermal delivery system provides an in-vitro cumulative amount of permeation of from about 63 μg/cm² to about 388 μg/cm² of the transdermal delivery system surface area at 24 hours; from about 105 μg/cm² to about 660 μg/cm² of the transdermal delivery system surface area at 48 hours; and from about 139 μg/cm² to about 854 μg/cm² of the transdermal delivery system surface area at 72 hours; and from about 162 μg/cm² to about 955 μg/cm² of the transdermal delivery system surface area at 96 hours; as determined via an in-vitro permeation test utilizing a Valia-Chien cell where the membrane is a human cadaver skin and said cell has a receptor chamber containing a 40:60 mixture of ethanol:water.

15. The transdermal delivery system according to claim 10, wherein the backing layer is composed of a flexible material.

16. The transdermal delivery system according to claim 10, wherein the backing layer is selected from the group consisting of a flexible material, an inflexible material, and an aluminum foil.

17. The transdermal delivery system according to claim 10, wherein the polymeric matrix is at least one of rubber, a synthetic homo-, co- or blockpolymer, a urethane and silicone.

18. The transdermal delivery system according to claim 10, wherein the softening agent is at least one of dodecanol, undecanol, octanol, a glycol and glycanol.

19. The transdermal delivery system according to claim 10, wherein the solvent is a monoester of a dicarboxylic acid.

20. The transdermal delivery system according to claim 10, wherein the solvent is at least one of monomethyl glutarate and monomethyl adipate.

21. The transdermal delivery system according to claim 10, wherein by weight the polymer is present in about 55%, the loratadine in about 10%, the solvent in about 10% and the softener in about 15%.

22. The transdermal delivery system according to claim 10, wherein the solvent is present in from about 25 to 100% the weight of the loratadine.

23. The transdermal delivery system according to claim 10, which also comprises a removable protective layer.

24. The transdermal delivery system according to claim 10, wherein the pressure-sensitive adhesive reservoir layer comprises a polymer based on an acrylate, a methacrylate, a silicone compound or a combination thereof.

25. The transdermal delivery system according to claim 10, wherein the softening agent is a medium-chain triglyceride of the caprylic/capric acids of coconut oil.

26. The transdermal delivery system according to claim 10, wherein the solvent has at least one acidic group.

27. A method of effectively treating seasonal allergic rhinitus, chronic idiopathic urticaria, or both conditions in a human patient, comprising administering loratadine transdermally to the human patient by applying a transdermal delivery system containing loratadine or a pharmaceutically acceptable salt thereof to the skin of a patient, and maintaining said transdermal delivery system in contact with the skin of the patient for at least 5 days, said transdermal delivery system maintaining an effective mean relative release rate to provide a therapeutic blood level of said loratadine within three days from the initiation of the dosing interval, and thereafter maintaining a therapeutic blood level until the end of at least the five-day dosing interval, said transdermal delivery device maintaining a plasma level of loratadine at steady state of about 3 ng/ml;

said transdermal delivery device comprising a backing layer which is substantially impermeable to the loratadine or pharmaceutically acceptable salt thereof; and a reservoir layer consisting essentially of 20 to 90% by weight of a polymeric matrix, 0.1 to 30% by weight of a softening agent; 0.1 to 20% by weight of loratadine base or of a pharmaceutically acceptable salt thereof and 0.1 to 30% by weight of a solvent, for the loratadine or salt thereaof;

said transdermal delivery system having a mean relative release rate of from about 2.8 μg/cm²/hr to about 16.2 μg/cm²/hr of the transdermal delivery system surface area at 24 hours;

from about 2.3 μg/cm²/hr to about 13.7 μg/cm²/hr of the transdermal delivery system surface area at 48 hours;

from about 2.0 μg/cm²/hr to about 11.9 μg/cm²/hr of the transdermal delivery system surface area at 72 hours;

and a mean relative release rate of from about 1.8 μg/cm²/hr to about 9.9 μg/cm²/hr of the transdermal delivery system surface area at 96 hours; as determined via an in-vitro permeation test utilizing a Valia-Chien cell where the membrane is a human cadaver skin, said cell having a receptor chamber containing a 40:60 mixture of ethanol:water.

28. The method of claim 1, wherein said transdermal delivery system has a mean relative release rate of from about 1.5 μg/cm²/hr to about 8.5 μg/cm²/hr of the transdermal delivery system surface area at 120 hours;

from about 2.4 µg/cm²/hr to about 7.7 µg/cm²/hr of the transdermal delivery system surface area at 144 hours;

and from about 1.5 µg/cm²/hr to about 6.7 µg/cm²/hr of the transdermal delivery system surface area at 168 hours; as determined via an in-vitro permeation test utilizing a Valia-Chien cell where the membrane is a human cadaver skin, said cell having a receptor chamber containing a 40:60 mixture of ethanol:water.

29. The transdermal delivery system of claim 8, wherein said transdermal delivery system has a mean relative release rate of from about 1.5 µg/cm²/hr to about 8.5 µg/cm²/hr of the transdermal delivery system surface area at 120 hours;

from about 2.4 µg/cm²/hr to about 7.7 µg/cm²/hr of the transdermal delivery system surface area at 144 hours;

and from about 1.5 µg/cm²/hr to about 6.7 µg/cm²/hr of the transdermal delivery system surface area at 168 hours; as determined via an in-vitro permeation test utilizing a Valia-Chien cell where the membrane is a human cadaver skin, said cell having a receptor chamber containing a 40:60 mixture of ethanol:water.

30. The method of claim 27, wherein said transdermal delivery system has a mean relative release rate of from about 1.5 µg/cm²/hr to about 8.5 µg/cm²/hr of the transdermal delivery system surface area at 120 hours;

from about 2.4 µg/cm²/hr to about 7.7 µg/cm²/hr of the transdermal delivery system surface area at 144 hours;

and from about 1.5 µg/cm²/hr to about 6.7 µg/cm²/hr of the transdermal delivery system surface area at 168 hours; as determined via an in-vitro permeation test utilizing a Valia-Chien cell where the membrane is a human cadaver skin, said cell having a receptor chamber containing a 40:60 mixture of ethanol:water.

31. The method of claim 1, wherein a softening agent is selected from the group consisting of dodecanol, undecanol, octanol, a glycol, glycanol and a medium-chain triglyceride of the caprylic/capric acids of coconut oil; and the solvent is selected from the group consisting of a monoester of a dicarboxylic acid, monomethyl glutarate and monomethyl adipate.

32. The transdermal delivery system of claim 8, wherein a softening agent is selected from the group consisting of dodecanol, undecanol, octanol, a glycol, glycanol and a medium-chain triglyceride of the caprylic/capric acids of coconut oil; and the solvent is selected from the group consisting of a monoester of a dicarboxylic acid, monomethyl glutarate and monomethyl adipate.

33. The method of claim 27, wherein a softening agent is selected from the group consisting of dodecanol, undecanol, octanol, a glycol, glycanol and a medium-chain triglyceride of the caprylic/capric acids of coconut oil; and the solvent is selected from the group consisting of a monoester of a dicarboxylic acid, monomethyl glutarate and monomethyl adipate.

34. The method of claim 1, wherein the transdermal delivery system comprises a solution of the loratadine or a pharmaceutically acceptable salt thereof.

35. The transdermal delivery system of claim 8, wherein the transdermal delivery system comprises a solution of the loratadine or a pharmaceutically acceptable salt thereof.

36. The method of claim 27, wherein the transdermal delivery system comprises a solution of the loratadine or a pharmaceutically acceptable salt thereof.

37. The method of claim 1, wherein said loratadine is the only active agent in the transdermal delivery system.

38. The transdermal delivery system of claim 8, wherein said loratadine is the only active agent in the transdermal delivery system.

39. The method of claim 27, wherein said loratadine is the only active agent in the transdermal delivery system.

* * * * *